(12) United States Patent
Colvin, Jr.

(10) Patent No.: US 6,794,195 B2
(45) Date of Patent: Sep. 21, 2004

(54) DETECTION OF ANALYTES IN AQUEOUS ENVIRONMENTS

(75) Inventor: Arthur E. Colvin, Jr., Mt. Airy, MD (US)

(73) Assignee: Sensors for Medicine & Science, Inc., Germantown, MD (US)

(*) Notice: Subject to any disclaimer, the term of this patent is extended or adjusted under 35 U.S.C. 154(b) by 0 days.

(21) Appl. No.: 09/920,627

(22) Filed: Aug. 3, 2001

(65) Prior Publication Data

US 2002/0039793 A1 Apr. 4, 2002

Related U.S. Application Data

(63) Continuation-in-part of application No. 09/632,624, filed on Aug. 4, 2000, now abandoned.

(51) Int. Cl.$^7$ ............................................... G01N 33/00
(52) U.S. Cl. ........................... 436/95; 436/94; 436/73; 436/81; 436/172; 548/110; 534/15
(58) Field of Search .............................. 436/94, 73, 81, 436/95, 172; 548/110; 534/15

(56) References Cited

U.S. PATENT DOCUMENTS

| | | | |
|---|---|---|---|
| 6,002,954 A | * 12/1999 | Van Antwerp et al. | ..... 600/310 |
| 6,011,984 A | 1/2000 | Van Antwerp et al. | |
| 6,344,360 B1 | * 2/2002 | Colvin et al. | ............... 436/166 |

OTHER PUBLICATIONS

Appleton, B. et al., "Detection of Total Sugar Concentration Using Photoinduced Electron Transfer Materials: Development of Operationally Stable, Reusable Optical Errors", *Sensors and Actuators*, 2000, pp. 302–304.

Aoki, T. et al., "Effect of Phenylboronic Acid Groups in Copolymers on Endothelial Cell Differentiation into Capillary Structures", *J. Biomater. Sci. Polymer Edn*, 1997, vol. 9., No. 1, pp. 1–14.

Burgemeister, T., et al., "Fast Thermal Breaking and Formation of a B–N Bond in 2–(Aminomethyl)benzeneboronates," *Chem. Ber.*, 1981, vol. 114, pp. 3403–3411.

Hisamitsu, I. et al., "Glucose–Responsive Gel from Phenylborate Polymer and Poly(Vinyl Alcohol): Prompt Response at Physiological pH Through the Interaction of Borate with Amino Group in the Gel", *Phamaceutical Research*, 1997, vol. 14, No. 3, pp. 289–293.

Kataoka, K. et al., "Novel Sensing System for Glucose Based on the Complex Formation Between Phenylborate and Fluorescent Diol Compounds", *J. Biochem.*, 1995, vol. 117, pp. 1145–1147.

Kataoka, K. et al., "Totally Synthetic Polymer Gels Responding to External Glucose Concentration: Their Preparation and Application to On–Off Regulation of Insulin Release", *J. Am. Chem. Soc.*, 1998, vol. 120, pp. 12694–12695.

(List continued on next page.)

*Primary Examiner*—Jill Warden
*Assistant Examiner*—Monique T. Cole
(74) *Attorney, Agent, or Firm*—Rothwell, Figg, Ernst & Manbeck; Michael J. Moran

(57) ABSTRACT

The invention relates to indicator molecules for detecting the presence or concentration of an analyte in a medium, such as a liquid, and to methods for achieving such detection. More particularly, the invention relates to copolymer macromolecules containing relatively hydrophobic indicator component monomers, and hydrophilic monomers, such that the macromolecule is capable of use in an aqueous environment.

65 Claims, 9 Drawing Sheets

OTHER PUBLICATIONS

Kitano, S., et al., "Glucose–Responsive Complex Formation Between Poly(vinyl alcohol) and Poly(N–vinyl–2–pyrrolidone) with Pendent Phenylboronic Acid Moieties", *Makromol. Chem. Rapid Commun.*, 1991, vol. 12, pp. 227–233.

Kikuchi, A., et al., "Glucose–Sensing Electrode Coated with Polymer Complex Gel Containing Phenylboronic Acid", *Anal. Chem.*, 1996, vol. 68, pp. 823–828.

Peterson, J. et al., "Fiber Optic pH Probe for Physiological Use", *Anal. Chem.*, 1980, vol. 52, pp. 864–869.

Sandanayake, K., et al., "Two Dimensional Photoinduced Electron Transfer (PET) Fluorescence Sensor for Saccharides", *Chemistry Letters*, 1995, pp. 503–504.

Shino, D., et al., "Amine Effect on Phenylboronic Acid Complex with Glucose Under Physiological pH in Aqueous Solution", *J. Biomater. Sci. Polymer Edn.*, 1996, vol. 7, No. 8, pp. 697–705.

Soundararajan, S., et al., "Boronic Acids for Affinity Chromatography; Spectral Methods for Determinations of Ionization and Diol–Binding Constants", *Anal. Bio.*, 1989, vol, 178., pp. 125–134.

Vo–Dinh, T., et al., "Gel–Based Indo–1 Probe for Monitoring Calcium(II) Ions", *Anal. Chem.*, 1994, vol. 66, pp. 813–817.

Wang, W., et al., "Building Fluorescent Sensors by Template Polymerization: The Preparation of a Fluorescent Sensor for D–Fructose", *Organic Letters*, 1999, vol. 1, No. 8, pp. 1209–1212.

Weith, H., et al., "Synthesis of Cellulose Derivatives Containing the Dihydroxyboryl Group and a Study of Their Capacity to Form Specific Complexes with Sugars and Nucleic Acid Components", *Biochemistry*, 1970, vol. 9, No. 22, pp. 4396–4401.

Wulff, G., "Selective Binding to Polymers Via Covalent Bonds. The Construction of Chiral Cavities as Specific Receptor Sites", *Pure & Appl. Chem.*, 1982, vol. 54, No. 11, pp. 2093–2102.

Wulff, G., "Racemic Resolution of Free Sugars with Macroporous Polymers Prepared by Molecular Imprinting. Selectivity Dependence on the Arrangement of Functional Groups versus Spatial Requirements", *J. Org. Chem.*, 1991, vol. 56, pp. 395–400.

Wulff, G., "The Role of Binding–site Interactions in the Molecular Imprinting of Polymers", *Tibtech*, 1993, vol. 11, pp. 85–87.

Yurkevich, A., et al., Study of the Interaction of Polyols with Polymers Containing N–Substituted [(4–Boronophenyl)M-ethyl]–Ammonio Groups, *Carbohydrate Research*, 1975, vol. 43, pp. 215–224.

* cited by examiner

DETECTION OF ANALYTES IN AQUEOUS ENVIRONMENTS

CROSS-REFERENCE TO RELATED APPLICATIONS

This application is a continuation-in-part of application Ser. No. 09/632,624, filed Aug. 4, 2000, now abandoned.

STATEMENT REGARDING FEDERALLY SPONSORED RESEARCH OR DEVELOPMENT

Not applicable.

BACKGROUND OF THE INVENTION

1. Field of the Invention

This invention relates to indicator molecules for detecting the presence or concentration of an analyte in a medium, such as a liquid, and to methods for achieving such detection. More particularly, the invention relates to copolymer macromolecules containing relatively hydrophobic indicator component monomers, and hydrophilic monomers, such that the macromolecule is capable of use in an aqueous environment.

2. Description of the Related Art

Indicator molecules for detecting the presence or concentration of an analyte in a medium are known. Unfortunately, many of such indicators are insoluble or sparingly soluble in water. For example, U.S. Pat. No. 5,503,770 (James, et al.) describes a fluorescent boronic acid-containing compound that emits fluorescence of a high intensity upon binding to saccharides, including glucose. The fluorescent compound has a molecular structure comprising a fluorophore, at least one phenylboronic acid moiety and at least one amine-providing nitrogen atom where the nitrogen atom is disposed in the vicinity of the phenylboronic acid moiety so as to interact intramolecularly with the boronic acid. Such interaction thereby causes the compound to emit fluorescence upon saccharide binding. See also T. James, et al., *J. Am. Chem. Soc.* 117(35):8982–87 (1995). However, the compound described in example 2 of U.S. Pat. No. 5,503,770 (having formula (6)) is substantially insoluble in water, and as a practical matter requires the presence of an organic solvent such as methanol in order to work in a liquid environment.

Lack of sufficient aqueous solubility is a severe problem when dealing with applications in an aqueous environment, for example, in vivo applications. Thus, there remains a great need for adapting insoluble or sparingly soluble indicators for use in aqueous environments.

BRIEF SUMMARY OF THE INVENTION

In one aspect, the present invention is directed to an indicator macromolecule for detecting the presence or concentration of an analyte in an aqueous environment, said macromolecule comprising a copolymer of:
  a) one or more indicator component monomers which individually are not sufficiently water soluble to permit their use in an aqueous environment for detecting the presence or concentration of said analyte; and
  b) one or more hydrophilic monomers;
such that the macromolecule is capable of detecting the presence or concentration of said analyte in an aqueous environment.

In another aspect, the present invention is directed to a method for the production of an indicator macromolecule for detecting the presence or concentration of an analyte in an aqueous environment, said method comprising copolymerizing:
  a) one or more indicator component monomers which individually are not sufficiently water soluble to permit their use in an aqueous environment for detecting the presence or concentration of said analyte; and
  b) one or more hydrophilic monomers;
such that the resulting macromolecule is capable of detecting the presence or concentration of said analyte in an aqueous environment.

In another aspect, the present invention is directed to a method for detecting the presence or concentration of an analyte in a sample having an aqueous environment, said method comprising:
  a) exposing the sample to an indicator macromolecule, said macromolecule comprising a copolymer of:
    i) one or more indicator component monomers which individually are not sufficiently water soluble to permit their use in an aqueous environment for detecting the presence or concentration of said analyte; and
    ii) one or more hydrophilic monomers;
  such that the resulting macromolecule is capable of detecting the presence or concentration of said analyte in an aqueous environment, and wherein the indicator macromolecule has a detectable quality that changes in a concentration-dependent manner when said macromolecule is exposed to said analyte; and
  b) measuring any change in said detectable quality to thereby determine the presence or concentration of said analyte in said sample.

In another aspect, the present invention provides a macromolecule which is capable of exhibiting an excimer effect, which comprises a copolymer of:
  a) one or more excimer forming monomers, the molecular constituents of which are capable of exhibiting an excimer effect when suitably oriented with respect to each other; and
  b) one or more other monomers;
such that the resulting macromolecule exhibits said excimer effect.

In yet another aspect, the present invention provides a method for producing a macromolecule which is capable of exhibiting an excimer effect, which method comprises copolymerizing:
  a) one or more excimer forming monomers, the molecular constituents of which are capable of exhibiting an excimer effect when suitably oriented with respect to each other; and
  b) one or more other monomers;
such that the resulting macromolecule exhibits said excimer effect.

In yet another aspect, the present invention provides a method for detecting the presence or concentration of an analyte in a sample, said method comprising:
  a) exposing the sample to an indicator macromolecule, said macromolecule comprising a copolymer of:
    i) one or more indicator component monomers, the molecules of which are capable of exhibiting an excimer effect when suitably oriented with respect to each other, and which are also capable of detecting the presence or concentration of an analyte; and
    ii) one or more other monomers;
such that the resulting macromolecule exhibits said excimer effect, and wherein the indicator macromolecule has a detectable quality that changes in a concentration-dependent manner when said macromolecule is exposed to said analyte; and b) measuring any change in said detectable quality to thereby determine the presence or concentration of said analyte in said sample.

DETAILED DESCRIPTION OF THE INVENTION

Figure 1:
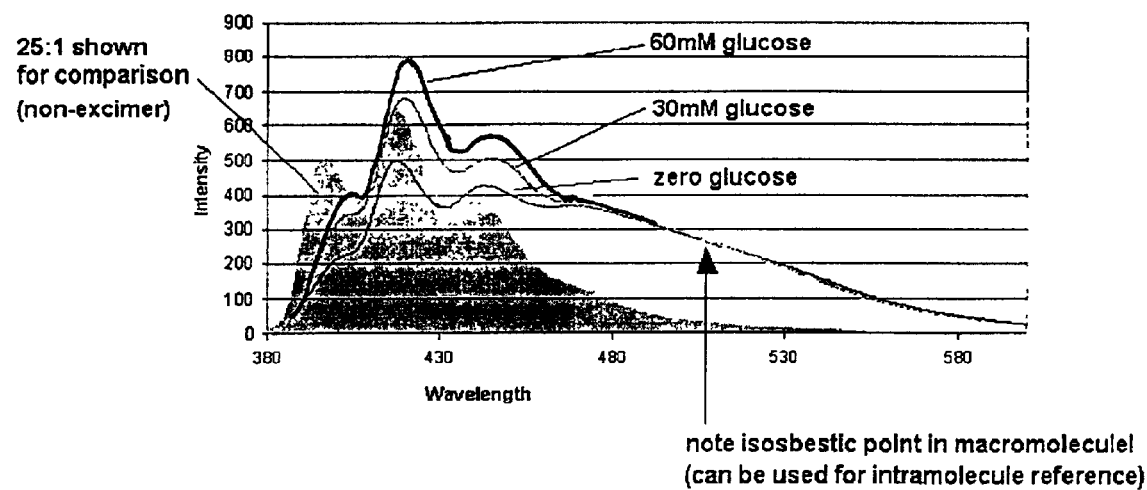
FIGS. 1–2 illustrate the emission spectra of several indicator macromolecules of the present invention as described in Example 2.

In one aspect, the present invention provides a way to utilize, in an aqueous environment, indicator components which by themselves are insoluble or sparingly soluble in an aqueous environment. Such indicators are, in effect, copolymerized with one or more monomers which are sufficiently hydrophilic such that the resulting indicator macromolecule is sufficiently hydrophilic overall so as to overcome the hydrophobic contribution of the indicator component monomers.

Suitable indicator components include indicator molecules which are insoluble or sparingly soluble in water, and whose analyte is at least sparingly soluble in water. Suitable analytes include glucose, fructose and other vicinal diols; α-hydroxy acids; β-keto acids; oxygen; carbon dioxide; various ions such as zinc, potassium, hydrogen (pH measurement), carbonate, toxins, minerals, hormones, etc. It will be appreciated that within the scope of indicator component monomer as used herein are included mixtures of two or more individual monomers (at least one of which is not sufficiently soluble to function adequately in an aqueous environment) which, when incorporated into the macromolecules of the present invention, function as an indicator.

Many such indicator components are known. For example, the compounds depicted in U.S. Pat. No. 5,503,770 are useful for detecting saccharides such as glucose, but are sparingly soluble to insoluble in water. Other classes of indicators include the lanthanide chelates disclosed in copending U.S. application Ser. No. 09/265,979 filed Mar. 11, 1999 (and published as PCT International Application WO 99/46600 on Sep. 16, 1999), incorporated herein by reference; polyaromatic hydrocarbons and their derivatives; the indicators disclosed in co-pending application Ser. No. 09/754,217 filed Jan. 5, 2001 and application Ser. No. 60/269,887 filed Feb. 21, 2001, both of which describe indicators having two recognition elements capable of discriminating between glucose and interfering α-hydroxy acids or β-diketones, etc.

The indicator components of the present invention will generally have a detectable quality that changes in a concentration-dependent manner when the macromolecule is exposed to the analyte to be measured. Many such qualities are known and may be used in the present invention. For example, the indicator may include a luminescent (fluorescent or phosphorescent) or chemiluminescent moiety, an absorbance based moiety, etc. The indicator may include an energy donor moiety and an energy acceptor moiety, each spaced such that there is a detectable change when the macromolecule interacts with the analyte. The indicator may include a fluorophore and a quencher, configured such that the fluorophore is quenched by the quencher when the analyte is absent. In that situation, when the analyte is present, the indicator undergoes a configurational change which causes the quencher to move sufficiently distant from the fluorophore so that fluorescence is emitted. Conversely, the fluorophore and quencher may be configured such that in the absence of analyte, they are sufficiently separated and the fluorophore emits fluorescence; upon interaction with the analyte, the fluorophore and quencher are moved in sufficient proximity to cause quenching. The configurational change concept is described in more detail in co-pending application Ser. No. 09/754,219, filed Jan. 5, 2001, entitled "Detection of Analytes", incorporated herein by reference.

Other detectable moieties include those whose fluorescence is affected by analyte interaction via photoinduced electron transfer or inductive effects. These include the lanthanide chelates disclosed in copending U.S. application Ser. No. 09/265,979 filed Mar. 11, 1999 (and published as PCT International Application WO 99/46600 on Sep. 16, 1999), incorporated herein by reference; polyaromatic hydrocarbons and their derivatives; coumarins; BODIPY® (Molecular Probes, Eugene, Oreg.); dansyl; catechols; etc. Another class of moieties include those whose absorbance spectrum changes upon interaction of the indicator compound with the analyte, including Alizarin Red, etc. Another class of moieties include those whose fluorescence is modulated by proximity effects, e.g., energy donor/acceptor pairs such as dansyl/dabsyl, etc.

Preferably, the detectable quality is a detectable optical or spectral change, such as changes in absorptive characteristics (e.g., absorptivity and/or spectral shift), in fluorescent decay time (determined by time domain or frequency domain measurement), fluorescent intensity, fluorescent anisotropy or polarization; a spectral shift of the emission spectrum; a change in time-resolved anisotropy decay (determined by time domain or frequency domain measurement), etc.

Suitable hydrophilic monomers should be sufficiently hydrophilic so as to overcome the sum of the hydrophobic indicator component monomers, such that the resultant indicator macromolecule is capable of functioning in an aqueous environment. It will be readily apparent that a wide variety of hydrophilic monomers are suitable for use in the present invention. For example, suitable hydrophilic monomers include methacrylamides, methacrylates, methacrylic acid, dimethylacrylamide, TMAMA, vinyls, polysaccharides, polyamides, polyamino acids, hydrophilic silanes or siloxanes, etc., as well as mixtures of two or more different monomers.

Suitable hydrophilic monomers for a given application will vary according to a number of factors, including intended temperature of operation, salinity, pH, presence and identity of other solutes, ionic strength, etc. It would be readily apparent that the degree of hydrophilicity of the hydrophilic monomer or the indicator macromolecule can be increased by adding additional functional constituents such as ions (e.g., sulfonate, quartenary amine, carboxyl, etc.), polar moieties (e.g., hydroxyl, sulfhydryl, amines, carbonyl, amides, etc.), halogens, etc.

It will be appreciated that the molar ratio of hydrophilic monomer to indicator component monomer may vary widely depending on the specific application desired. Preferred ratios of hydroplilic monomer:indicator component monomer range from about 2:1 to about 1000:1, more preferably from about 5:1 to about 50:1.

The indicator macromolecules of the present invention may generally be synthesized by simply copolymerizing at least one indicator component monomer with at least one hydrophilic monomer. Optimum polymerization conditions (time, temperature, catalyst, etc.) will vary according to the specific reactants and the application of the final product, and can easily be established by one of ordinary skill.

It will be appreciated that the indicator macromolecules of the present invention may have any desired extent of water solubility. For example, the indicator macromolecule of Examples 1 and 2 below is very soluble, readily dissolving in aqueous solution. On the other hand, indicator macromolecules containing, for example, the hydrophilic monomer HEMA (hydroxyethyl methacrylate) or other common hydrogel constituents, can be non-soluble yet hydrophilic.

The soluble indicator macromolecules may be used directly in solution if so desired. On the other hand, if the desired application so requires, the indicator macromolecule may be immobilized (such as by mechanical entrapment, covalent or ionic attachment or other means) onto or within an insoluble surface or matrix such as glass, plastic, polymeric materials, etc. When the indicator macromolecule is entrapped within, for example, another polymer, the entrapping material preferably should be sufficiently permeable to the analyte to allow suitable interaction between the analyte and the indicator components in the macromolecule.

Many uses exist for the indicator macromolecules of the present invention, including uses as indicators in the fields of energy, medicine and agriculture. For example, the indicator macromolecules can be used as indicator molecules for detecting sub-levels or supra-levels of glucose in blood, tissues, urine, etc., thus providing valuable information for diagnosing or monitoring such diseases as diabetes and adrenal insufficiency. Medical/pharmaceutical production of glucose for human therapeutic application requires monitoring and control.

Uses for the present invention in agriculture include detecting levels of an analyte such as glucose in soybeans and other agricultural products. Glucose must be carefully monitored in critical harvest decisions for such high value products as wine grapes. As glucose is the most expensive carbon source and feedstock in fermentation processes, glucose monitoring for optimum reactor feed rate control is important in power alcohol production. Reactor mixing and control of glucose concentration also is critical to quality control during production of soft drinks and fermented beverages, which consumes the largest amounts of glucose and fermentable sugars internationally.

When the indicator macromolecules incorporate fluorescent indicator substituents, various detection techniques also are known in the art that can make use of the macromolecules of the present invention. For example, the macromolecules of the invention can be used in fluorescent sensing devices (e.g., U.S. Pat. No. 5,517,313) or can be bound to polymeric materials or other substrates such as test paper for visual inspection. This latter technique would permit, for example, glucose measurement in a manner analogous to determining pH with a strip of litmus paper. The macromolecules described herein may also be utilized as simple reagents with standard benchtop analytical instrumentation such as spectrofluorometers or clinical analyzers as made by Shimadzu, Hitachi, Jasco, Beckman and others. These molecules would also provide analyte specific chemical/optical signal transduction for fiber optic-based sensors and analytical fluorometers as made by Ocean Optics (Dunedin, Fla.), or Oriel Optics.

U.S. Pat. No. 5,517,313, the disclosure of which is incorporated herein by reference, describes a fluorescence sensing device in which the macromolecules of the present invention can be used to determine the presence or concentration of an analyte such as glucose or other vicinal diol compound in a liquid medium. The sensing device comprises a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, or in a waveguide upon which the indicator matrix is disposed, such that incident light from the light source causes the indicator molecules to fluoresce. The high-pass filter allows emitted light to reach the photodetector, while filtering out scattered incident light from the light source.

The fluorescence of the indicator molecules employed in the device described in U.S. Pat. No. 5,517,313 is modulated, e.g., attenuated or enhanced, by the local presence of an analyte such as glucose or other cis-diol compound.

In the sensor described in U.S. Pat. No. 5,517,313, the material which contains the indicator molecule is permeable to the analyte. Thus, the analyte can diffuse into the material from the surrounding test medium, thereby affecting the fluorescence emitted by the indicator molecules. The light source, indicator molecule-containing material, high-pass filter and photodetector are configured such that at least a portion of the fluorescence emitted by the indicator molecules impacts the photodetector, generating an electrical signal which is indicative of the concentration of the analyte (e.g., glucose) in the surrounding medium.

In accordance with other possible embodiments for using the indicator macromolecules of the present invention, sensing devices also are described in U.S. Pat. Nos. 5,910,661, 5,917,605 and 5,894,351, all incorporated herein by reference.

The macromolecules of the present invention can also be used in an implantable device, for example to continuously monitor an analyte in vivo (such as blood or tissue glucose levels). Suitable devices are described in, for example, co-pending U.S. patent application Ser. No. 09/383,148 filed Aug. 26, 1999, as well as U.S. Pat. Nos. 5,833,603, 6,002, 954 and 6,011,984, all incorporated herein by reference.

The macromolecules of the present invention have unique advantages. For example, absorbance of a sample is directly proportional to both the concentration of the absorber and the sample path length. Thus, in an absorbance-based assay, it is apparent that for a given level of absorbance, the sample path length may be greatly reduced if the absorber concentration is greatly increased. That desirable increase in concentration may be accomplished by decreasing the ratio of the hydrophilic monomer:indicator component monomer. In effect, the present invention allows the localized concentration of much more absorber component into a limited space, thereby increasing the absorbance per unit thickness. Thus the present invention additionally allows use of much smaller equipment when performing absorbance-based assays. It will also be apparent that for any optically-based assay, including fluorescence based assays, the ability to greatly increase the local concentration of the indicator component offers several advantages. For example, a higher local concentration of the indicator component can permit the utilization of thinner layers of indicator macromolecule, which in turn can greatly reduce the response time of the macromolecule to the presence or concentration of the analyte. Further, it can result in a higher extinction of excitation light, which can desirably reduce the incidence of autofluorescence when working in tissue systems or physiological solutions. For example, when working with a fluorescence based macromolecule, non-absorbed excitation light can interact with, e.g., NADH, tryptophan, tyrosine, etc. which may be present in tissue or physiological solutions resulting in undesirable interfering fluorescent emission from those moieties. Having a high local concentration of indicator component with high absorption can reduce that undesired interfering emission. Additionally, when utilizing an absorbance-based macromolecule in tissue or physiological solutions, it is desirable to reduce the amount of the source radiation that is reflected in potentially varying amounts by components in surrounding tissue or fluid, such as bilirubin, e.g. Therefore, having a high local concentration of indicator component with high absorption can reduce that undesired effect.

As a further aspect of the present invention, it has been discovered that certain macromolecules exhibit an excimer effect. By way of background, when two planar molecules with aromatic structure (such as is common with fluorophores) are concentrated to a point where their pi electron orbital lobes may overlap, a resonance condition can then occur for some species where the resonance from overlap results in a hybrid (couplet) structure which is energy favorable and stable. These two planar molecules become oriented in a coplanar configuration like two slices of bread on a sandwich with their electron clouds overlapping between them. For fluorescent planar species, a characteristic downfield emission occurs relative to the uncoupled species at wavelength of substantially lower energy than the parent species. Molecules able to form such favorable resonant configurations are known as excimers. As used herein, an excimer effect refers to the resulting characteristic longer wavelength emission from excimers.

Some examples of typical excimer-forming polyaromatic hydrocarbons include anthracene and pyrene. There are many others. An example is the anthracene derivative (boronate included), the indicator component used in Examples 1 and 2 of the present application. Although anthracene is known to form excimers in solution, one must be able to concentrate the molecule to sufficiently high levels to observe any excimer character. In the case of the anthracene derivative of Examples 1 and 2, the molecule is insoluble in water and insufficiently soluble in a solvent such as methanol to observe excimer characteristics. In the present examples, the relative concentration of the anthracene derivative monomer was increased in proportion to the hydrophilic monomer in the copolymer from 500:1, 400:1, 200:1, 100:1, 50:1, 25:1, 15:1 and then 5:1. All have the characteristic blue emission at 417 nm of the anthracene derivative except at 5:1 ratio, a green emission suddenly appears. This green emission is that of an excimer hybrid and the emission has been shifted downfield by approximately 100+ nanometers (~515–570 nm, green). The concentration of the overall solution does not need to be high since the distance between planar species is being controlled by placement along the polymer backbone rather than soluble concentration in 3-D space.

Surprisingly, it has been found that the excimer emission region is not responsive to changes in analyte concentration, but is responsive to all other aspects of the system analyzed, such as excitation intensity, temperature, and pH. As a result, the present indicator macromolecules may serve as both an indicator and an internal reference. For example, an ideal referencing scheme is one where the emission intensity at an indicator wavelength (i.e., the wavelength influenced by the analyte) is divided optically using select bandpass filters, by the emission intensity at the excimer wavelength. The resultant value corrects for interfering factors which affect fluorescent emission properties, such as fluorescent quenching by, e.g., oxygen, drift and error in pH, power factors and drift affecting LED intensity, ambient temperature excursions, etc.

It will be readily appreciated that the macromolecules of the present invention which exhibit an excimer effect will be useful in both aqueous and non-aqueous environments. Consequently, those macromolecules, as well as the component monomers (excimer-forming and other monomer), may range from hydrophilic to hydrophobic, depending upon the desired application.

Also, when the excimer macromolecules of the present invention are used to detect the presence or concentration of an analyte, the macromolecule may be used directly in solution, or may be immobilized as described above.

The macromolecules of the present invention can be prepared by persons skilled in the art without an undue amount of experimentation using readily known reaction mechanisms and reagents, including reaction mechanisms which are consistent with the general procedures described below.

EXAMPLE 1 a) Preparation of 9-[(methacryloylaminopropylamino)methyl]anthracene (A) One-Phase To a suspension of N-(3-aminopropyl) methacrylamide hydrochloride (Polysciences, #21200) (11.82 g, 0.066 mole, 3.0 eq) and a trace of inhibitor DBMP (2,6-di-t-butyl-4-methylphenol) (10 mg) in chloroform (250 mL) stirring in an ice-water bath, diisopropylethylamine (25 mL, 18.55 g. 0.144 mole, 6.5 eq) was added dropwise in 20 minutes. The mixture was allowed to warm up to room temperature and cooled again in ice-water bath. A clear solution of 9-chloromethylanthracene (5.0 g, 0.022 mole) in chloroform (100 mL) was added dropwise over 1 hour. It was run at 25° C. for 1 hour, 50° C. for 12 hours and then 70° C. for 2 hours.

The mixture was washed with water (60 mL×4), and the aqueous layer was extracted with methylene chloride. The organic layers were combined, dried over $Na_2SO_4$, separated, and the solvent was removed under reduced pressure at 40° C. The crude material was then chromatographed on silica gel with 2–5% methanol in methylene chloride to give 2.44 g (33.4%) of product as a solid. TLC (silica gel): $R_f$ 0.39 ($MeOH/CH_2Cl_2$=1/9), a single spot.

(B) Two-Phase

To a clear solution of N-(3-aminopropyl) methacrylamide hydrochloride (788 mg, 4.41 mmole, 10 eq) and a trace of inhibitor MEHQ (methylether hydroquinone) (2 mg) in a mixture of water (30 mL) and tetrahydrofuran (30 mL) stirring in an ice-water bath. A $Na_2CO_3/NaHCO_3$ buffer (66 mL, 0.2 M, pH 10) was added in 1 hour and a solution of 9-chloromethylanthracene (100 mg, 0.441 mmole) in chloroform (100 mL) was added in 3 hours. It was run at 25° C. for 7 hours and then 55° C. for 12 hours.

The organic layer was separated, washed with water (50 mL×4), and the aqueous layers were extracted with methylene chloride. The organic layers were combined, dried over $Na_2SO_4$, separated, and the solvent was removed with reduced pressure at 45° C. The crude material (270 mg) was then chromatographed on silica gel with 10–20% methanol in methylene chloride to give 28.7 mg (19.6% of product as a solid TLC (silica gel): $R_f$ 0.77 ($MeOH/CH_2Cl_2$=3/7), a single spot.

b) Preparation of 9-[[N-methacryloylaminopropyl-N-(o-boronobenzyl)amino]methyl]anthracene To a solution of the product obtained in step a) above (2.440 g, 0.00734 mole) and a trace of inhibitor DBMP (10 mg) in chloroform (200 mL) stirring in an ice-water bath, DIEA (diisopropylethylamine) (2.846 g, 3.84 mL, 0.022 mole, 3.0 eq) was added by portions in 10 minutes, and then a solution of 2,2-dimethylpropane-1,3-diyl[o-(bromomethyl)phenyl]boronate (2.492 g, 0.00881 mole, 1.2 eq) in chloroform (15 mL) was added in 30 minutes. The reaction was run at room temperature for 20 hours.

The mixture was washed with water, separated and the aqueous layers were extracted with methylene chloride. The organic layers were combined, dried over $Na_2SO_4$, separated and the solvent was removed with reduced pressure at 25° C. The semi-solid (4.75 g) was then chromatographed on silica gel with 2–5% methanol in methylene chloride to give 2.50 g (76.3%) of product as a lightly yellow crystalline solid, mp 72–73° C., TLC (silica gel): $R_f$ 0.36 ($MeOH/CH_2Cl_2$=1/9). It is soluble in $CH_2Cl_2$, $CHCl_3$, THF, $CH_3OH$, and $C_2H_5OH$. Limited solubility in $H_2O$ and ether.

c) Preparation of water-soluble-copolymeric solutions of MAPTAC and 9-[[N-methacryloylaminopropyl-N-(o-boronobenzyl)amino]methyl]anthracene (50:1) solution: To a solution of the monomer (42.3 mg, 0.0908 mmole) in ethanol (100%, 1.5 mL), MAPTAC [3-(methacryloylamino)propyl]trimethylammonium chloride (2.0 mL, 1.0 g, 4.54 mmole, 50 eq) and an AIBN (azobisisobutyl nitrile) ethanolic solution (0.183 M, 0.2 mL) as radical initiator were added, a clear solution was obtained. It was saturated with nitrogen and then heated to 70° C. in 1 hour, and kept at 70° C. for 80 minutes, and a viscous liquid was obtained.

The liquid obtained was treated with water (26 mL) and filtered through a microfilter (0.45 um) to give a clear solution. After dialysis through a cellulose acetate membrane (MWCO 3500) with water 5 L×4), it was concentrated with polyethylene glycol (MW 20 K) to a clear solution (34.54 g). Concentration: 24.0 mg solid in 1.0 g solution, total solid 829 mg, yield 79.5%.

Similar procedures were applied to prepare copolymeric solutions of 500:1, 400:1, 200:1, 100:1, 50:1, 25:1, 15:1, and 5:1 molar ratios of hydrophilic monomer:indicator.

Glucose Modulation of 50:1 and 25:1 Co-Polymers

The modulation of the fluorescence of the 50:1 and 25:1 indicator macromolecules by glucose solutions having various concentrations is shown below in Tables 1 and 2. Table 1 shows the results using two different concentrations (15 mg/ml and 25 mg/ml) of the 25:1 indicator macromolecule of this example with four different glucose concentrations. Table 2 shows the results using two different concentrations (10 mg/ml and 20 mg/ml) of the 50:1 indicator macromolecule of this example with four different glucose concentrations. In both Tables, I/Io is the ratio of the emitted intensities at 420 nm after and before exposure to glucose (365 nm excitation).

TABLE 1

| Glucose concentration (mM) | I/Io for 15 mg/ml indicator macromolecule (25:1) | I/Io for 25 mg/ml indicator macromolecule (25:1) |
| --- | --- | --- |
| 0 | 1.00 | 1.00 |
| 50 | 1.44 | 1.50 |
| 100 | 1.75 | 1.90 |
| 200 | 2.13 | 2.33 |

TABLE 2

| Glucose concentration (mM) | I/Io for 10 mg/ml indicator macromolecule (50:1) | I/Io for 20 mg/ml indicator macromolecule (50:1) |
| --- | --- | --- |
| 0 | 1.00 | 1.00 |
| 50 | 1.40 | 1.48 |
| 100 | 1.70 | 1.79 |
| 200 | 2.04 | 2.22 |

EXAMPLE 2

This example demonstrates a surprising and useful excimer effect present in connection with the 5:1 indicator macromolecule prepared in Example 1.

FIG. 1 depicts the emission spectra of the 5:1 indicator macromolecule when exposed to three concentrations of glucose (0 mM, 30 mM and 60 mM) after excitement by light at 365 nm. Also shown in the shaded region of FIG. 1 is the emission of the non-excimer 25:1 indicator macromolecule from Example 1. The excimer emission region shows an "isosbestic region" rather than an isosbestic point. It can be seen from FIG. 1 that the excimer emission region (the region where the 0 mM, 30 mM and 60 mM glucose lines overlap) is not responsive to changes in glucose concentration (just like an isosbestic point). The excimer emission region begins approximately 100 nm downfield from the peak responsive wavelength of the anthracene derivative modulation. Except for glucose, the excimer is responsive to all other aspects of the system, such as excitation intensity, temperature, and pH. Therefore, an ideal referencing scheme is one where the amplitude or signal value at 415 nm is divided electronically by the amplitude or signal value at 515 nm or another wavelength or range of wavelengths within the excimer emission region, and the resultant value will be corrected for drift and error in pH, power factors and drift affecting LED intensity, ambient temperature excursions, etc. That is demonstrated below.

Demonstration of Excitation Intensity, Temperature and pH Correction

The glucose modulation of the 5:1 indicator macromolecule was measured with three different glucose solutions (0 mM, 100 mM and 200 mM). The emission spectra were determined for each of the glucose solutions at three different spectrophotometer slit configurations for source and emitted light (1.5 being narrower and 3 being wider). The data are shown in Table 3. In the Table, the ratio of the emission intensity at 420 nm to the emission intensity at 550 nm is relatively independent of slit configuration.

TABLE 3

| Slit Configuration | I420/I550 0 mN glucose | I420/I550 100 mN glucose | I420/I550 200 mM glucose |
| --- | --- | --- | --- |
| 1.5/1.5 | 3.92 | 6.18 | 7.36 |
| 1.5/3 | 3.93 | 6.12 | 7.25 |
| 3/3 | 4.00 | 6.27 | 7.28 |

The temperature stability of the 5:1 excimer indicator macromolecule was determined. The ratio of the emissions at 420 nm and 550 nm for a 1 mg/ml solution of the 5:1 excimer indicator macromolecule exposed to 200 mM glucose (pH 7.5) was 7.57 at room temperature and 7.53 at approximately 60° C.

Figure 2:
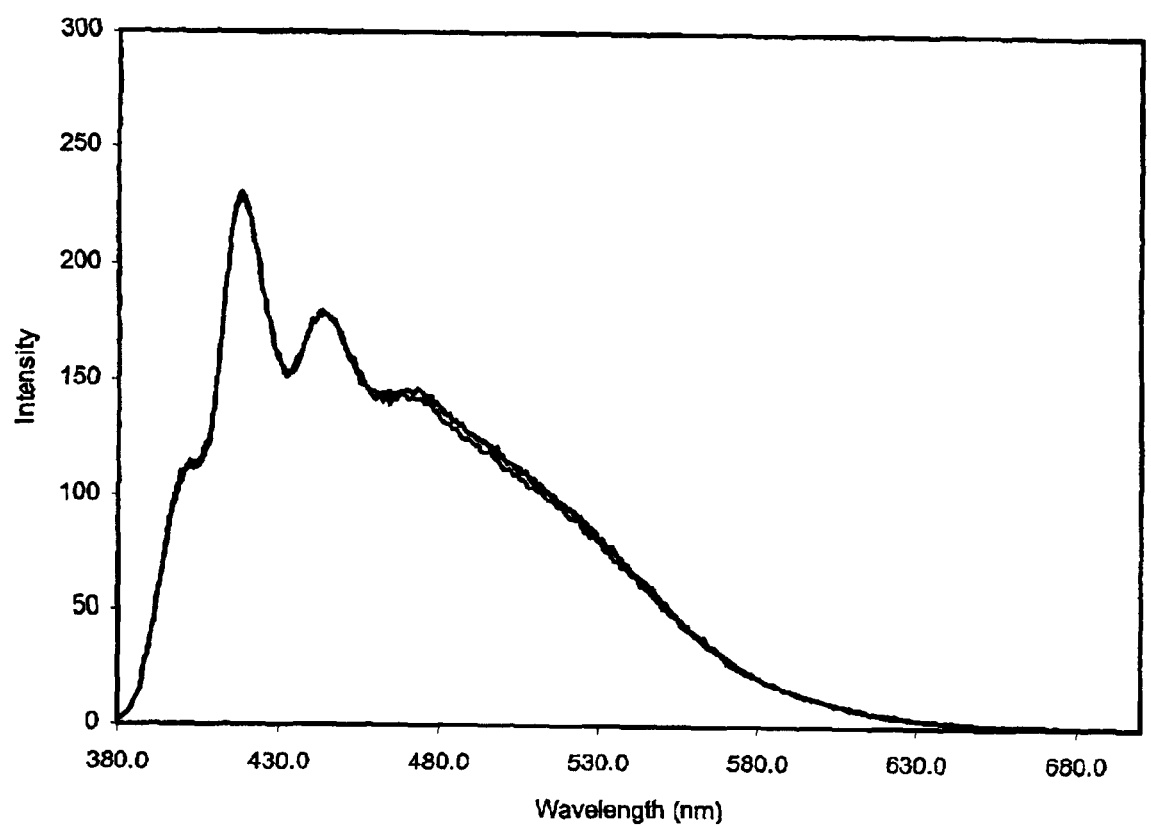

The pH stability of the 5:1 excimer indicator macromolecule was also determined. The ratio of the emissions at 420 nm and 550 nm for a 1 mg/ml solution of the 5:1 excimer indicator macromolecule at three different pH levels (6.5, 7.0 and 7.5) were determined (excitation light at 370 nm, slits 1.5,3), and are shown in Table 4. The full emission spectra are shown in FIG. 2. The variation over the range tested was statistically insignificant.

TABLE 4

| I420/I550 pH 6.5 | I420/I550 pH 7.0 | I420/I550 pH 7.5 |
| --- | --- | --- |
| 4.28 ± 0.18 | 4.60 ± 0.37 | 4.29 ± 0.19 |

It is believed that the stability of the excimer complex (presumably through the pi cloud) exceeds that of the non-excimer anthracene derivative, and, that the boronate recognition feature, which is able to perturb the properties of the non-excimer, and thus make a good indicator, is not able to perturb the more stable excimer complex and thus the excimer makes a very good reference indicator. The reference molecule is structurally unaltered from the read channel indicator. The polymer matrix may be the same, and in this example is in fact the same macromolecule. The recognition element is open and intact, but the inductive energy influence between recognition element and fluorophore center has been muted.

The foregoing is quite significant, because it can eliminate the need for separate physical and/or chemical environments between indicator and reference molecules.

EXAMPLE 3

Figure 3:
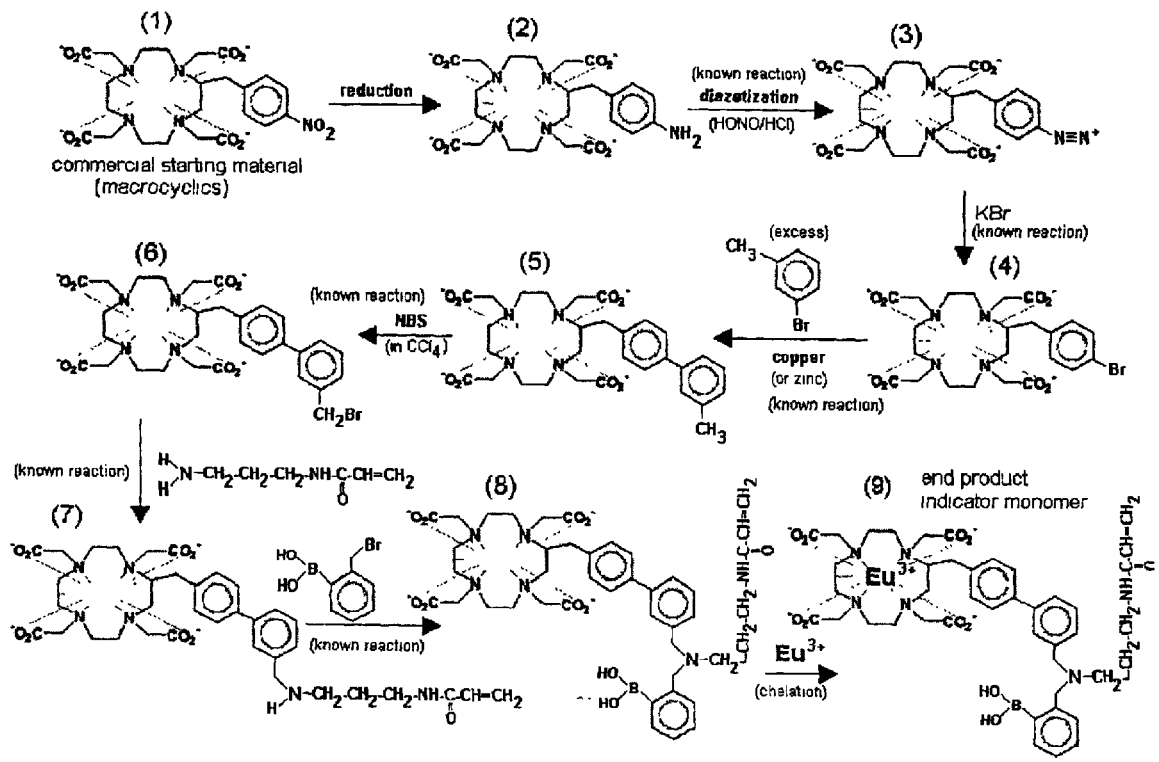
FIG. 3 depicts the synthesis of an indicator component monomer referred to in Example 3.

The synthesis of a suitable lanthanide chelate indicator component monomer is depicted in FIG. 3. Compounds (1) and (2) are commercially available from Macrocyclics, Richardson, Tex. (compound (2) is known as p-$NH_2$-Bz-DOTA). The end product (9) may be co-polymerized with one or more other monomers to form an indicator macromolecule.

EXAMPLE 4

Single-Methacrylamide Monomer of Bis-Boronate-Anthracene

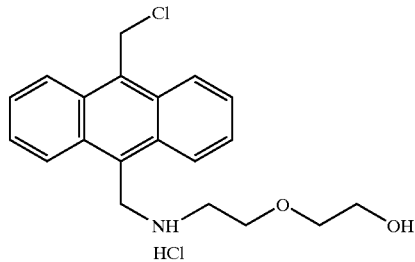

A. 9-chloromethyl-10-[[2-(2-hydroxyethoxy) ethylamino]-methyl]anthracene hydrochloride salt.

To a suspension of 9,10-bis(chloromethyl)anthracene (5.18 g, 18.8 mmole, 3.99 equiv.) in 200 mL of NMP was added 2-(2-aminoethoxy)ethanol (0.495 g, 0.475 mL, 4.71 mmole). The mixture was stirred in the dark for 17 hours. At this time, the reaction mixture was concentrated to ~50 mL under vacuum at 50° C. The residue was purified by silica gel chrom atography (150 g gravity grade silica gel, 0–10% $CH_3OH/CH_2Cl_2$) to yield 0.425 g (24%) of a yellow/orange solid.

TLC: Merck silica gel 60 plates, $R_f$ 0.72 with 70/30 $CH_2Cl_2/CH_3OH$, see with UV (254/366), ninhydrin stain.

HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 16.1 min.

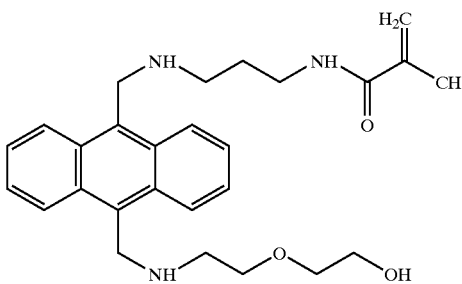

B. 9-[[2-(2-hydroxyethoxy)ethylamino]methyl]-10-[[(3-methacrylamido)propylamino]methyl]anthracene.

To a suspension of N-(3-aminopropyl)methacrylamide hydrochloride salt (3.08 g, 17.2 mmole, 4.2 equiv.), DIEA (5.19 g, 7.00 mL, 40.1 mmole, 9.8 equiv.) and ~3 mg of BHT in 125 mL $CHCl_3$ at 23° C. was added dropwise a solution of 9-chloromethyl-10-[[2-(2-hydroxyethoxy)ethylamino]-methyl]anthracene hydrochloride salt (1.56 g, 4.10 mmole) in 25 mL of $CHCl_3$. The mixture was subsequently stirred in the dark for 92 hours. At this time, the reaction mixture was filtered and washed with 2×40 mL of $NaHCO_3$ (saturated aqueous solution). The organic extract was dried over anhydrous $Na_2SO_4$, filtered and concentrated to yield a sticky orange solid which was purified by alumina chromatography (50 g activated neutral alumina, 0–5% $CH_3OH/CH_2Cl_2$) to yield 0.364 g (20%) of an orange solid.

TLC: Merck silica gel 60 plates, Rf 0.16 with 70/30 $CH_2Cl_2/CH_3OH$, see with UV (254/366), ninhydrin stain.

HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 16.85 min.

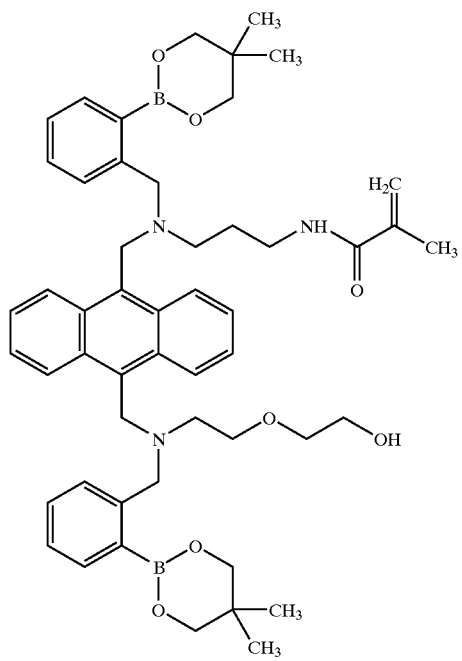

C. 9-[N-[2-(5,5-dimethyl-[1,3,2,]dioxaborinan-2-yl) benzyl]-N-[3-(methacrylamido)propylamino]methyl]-10-[N-[2-(5,5-dimethyl-[1,3,2]dioxaborinan-2-yl)benzyl]-N-[2-(2-hydroxyethoxy)-ethylamino]methyl]anthracene. (Single-methacrylamide monomer).

A solution of 9-[[2-(2-hydroxyethoxy)ethylamino]-methyl]-10-[[(3-methacrylamido)propylamino]methyl]-anthracene (0.343 g, 0.763 mmole), DIEA (0.965 g, 1.30 mL, 9.8 equiv.) and (2-bromomethylphenyl)boronic acid neopentyl ester (1.09 g, 3.85 mmole, 5.0 equiv.) in 20 mL $CHCl_3$ at 23° C. was stirred in the dark for 25 hours. At this time, the reaction mixture was concentrated initially by rotary evaporation, then using a vacuum pump to remove DIEA. The residue was purified by alumina column chromatography (40 g activated neutral alumina, 0–10% $CH_3OH/CH_2Cl_2$) to yield 0.299 g (46%) of a yellow orange solid. This product may be copolymerized with one or more other monomers to form an indicator macromolecule. The boronate groups should be deprotected prior to use.

FAB MS: Calc'd for $C_{51}H_{65}B_2N_3O_7$ $[M]^+$ 854; Found $[M+1]^+$ 855.

TLC: Merck basic alumina plates, Rf 0.35 with 95/5 $CH_2Cl_2/CH_3OH$, see with UV (254/366).

HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 19.7 min.

EXAMPLE 5

Dual-Methacrylamide Monomer of Bis-Boronate-Anthracene

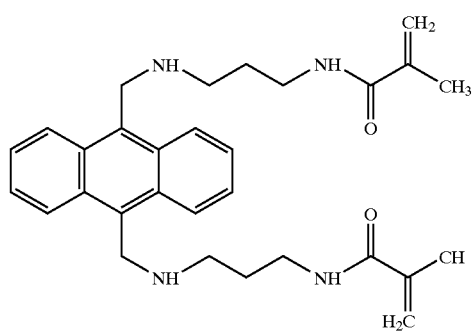

A. 9,10-bis[3-(methacrylamido)propylamino]methylanthracene.

A suspension of 9,10-bis(chloromethyl)anthracene (1.5 g, 5.45 mmole), DIEA (28.17 g, 38.00 mL, 218 mmole, 40 equiv.), N-(3-aminopropyl)methacrylamide hydrochloride salt (9.76 g, 54.5 mmole, 10.0 equiv.), and ~5 mg of BHT in 200 mL $CHCl_3$ at 23° C. was stirred in the dark for 4 days at 40° C. At this time, the temperature was increased to 45° C. and the mixture was stirred for 3 days longer. At this time, a precipitate had formed. The mixture was filtered, and the solid product dissolved in the minimum amount of $CH_2Cl_2$. A yellow crystalline solid, the bis hydrochloride salt of the desired product, formed overnight (3.15 g, quantitative).

TLC: Merck basic alumina plates, Rf 0.31 with 90/10 $CH_2Cl_2/CH_3OH$, see with UV (254/366).

HPLC: HP 1100 HPLC chromatograph, Waters 5×100 mm NovaPak HR C18 column, 0.100 mL injection, 0.75 mL/min, 360 nm detection, A=water (0.1% HFBA) and B=MeCN (0.1% HFBA), gradient 10% B 2 min, 10–80% B over 18 min, 80–100% B over 2 min, 100% B 2 min, retention time 15.0 min.

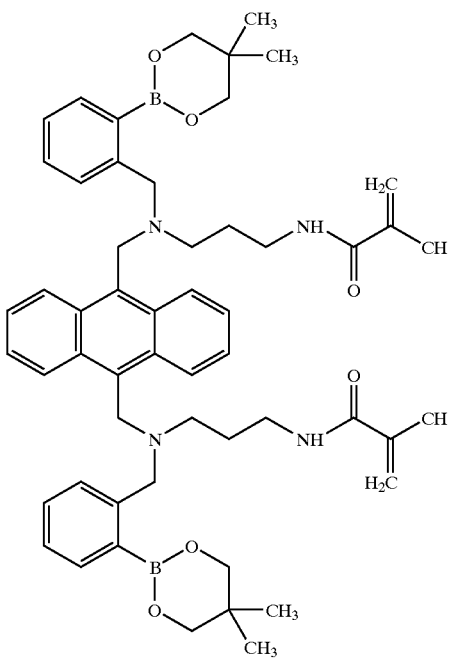

B. 9,10-bis[N-[2-(5,5-dimethyl-[1,3,2,]dioxaborinan-2-yl)benzyl]-N-[3-(methacrylamido)propylamino] methylanthracene.

A solution of 9,10-bis[3-(methacrylamido)-propylamino] methylanthracene (0.650 g, 1.34 mmole of the free amine), DIEA (0.612 g, 0.825 mL, 4.74 mmole, 3.55 equiv.), (2-bromomethylphenyl)boronic acid neopentyl ester (1.34 g, 4.74 mmole, 3.55 equiv.) and BHT (5 mg as inhibitor) in 20 mL $CHCl_3$ at 23° C. was stirred in the dark for 5 days. At this time, the reaction mixture was concentrated in vacuo and the residue was purified by alumina chromatography (200 g activated neutral alumina, 0–2% $CH_3OH/CH_2Cl_2$) to yield 0.465 g (39%) of a very viscous yellow oil.

TLC: Merck basic alumina plates, Rf 0.59 with 90/10 $CH_2Cl_2/CH_3OH$, see with UV (254/366).

HPLC: HP 1100 HPLC chromatograph, Waters 5×100 mm NovaPak HR C18 column, 0.050 mL injection, 0.75 mL/min, 360 nm detection, A=water (0.1% HFBA) and B=MeCN (0.1% HFBA), gradient 10% B 2 min, 10–80% B over 18 min, 80–100% B over 2 min, 100% B 2 min, retention time 16.9 min.

C. Preparation of N,N-Dimethylacrylamide Hydrogel with Glucose Indicator:

A solution of N,N-dimethylacrylamide (40% wt.) and N,N'-methylenebisacrylamide (0.8% wt.) in ethylene glycol was prepared. 9,10-bis[N-[2-(5,5-dimethyl-[1,3,2] dioxaborinan-2-yl) -benzyl]-N-]3-(methacrylamido)-propylamino]methylanthracene (17.8 mg, $2\times10^5$ mole) and 40 µL of aqueous ammonium persulfate (5% wt) were combined with 1 mL of ethylene glycol monomer solution. The resulting solution was placed in a glove box purged with nitrogen. An aqueous solution of N,N,N',N'-tetramethylethylenediamine (80 µL, 5% wt.) was added to the monomer formulation to accelerate polymerization. The resulting formulation was poured in a mold constructed from microscope slides and 100 micron stainless steel spacer. After being kept for 8 hours in nitrogen atmosphere the mold was placed in phosphate buffered saline (PBS) (10 mM PBS, pH=7.4), the microscope slides were separated, and the hydrogel was removed. The hydrogel was washed with 100 mL of PBS containing 1 mM lauryl sulfate sodium salt and 1 mM EDTA sodium salt for 3 days, the solution being changed every day, followed by washing with DMF/PBS (10/90 by vol., 3×100 mL), and finally with PBS (pH=7.4, 3×100 mL). The resulting hydrogel polymer was stored in PBS (10 mM PBS, pH=7.4) containing 0.2% wt. sodium azide and 1 mM EDTA sodium salt.

D. Modulation of Fluorescence With Glucose, Lactate and Acetoacetate

Figure 4:
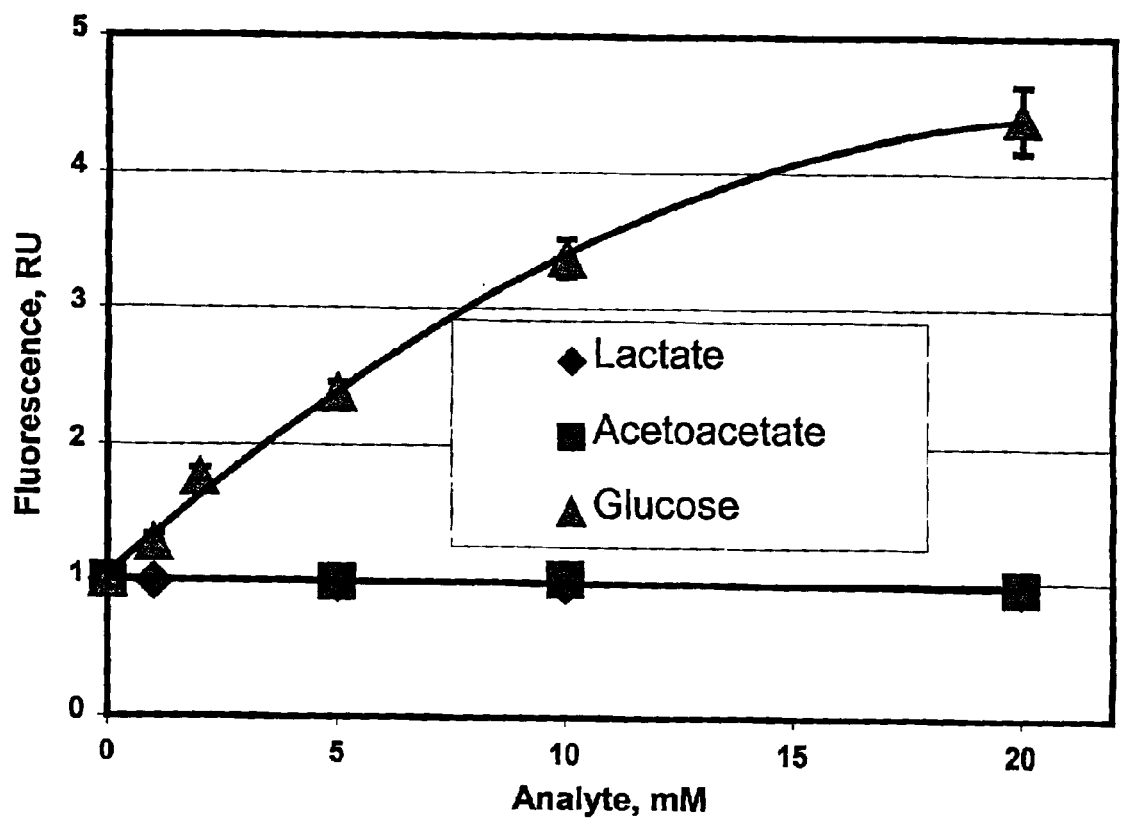
FIG. 4 illustrates the normalized fluorescence emission (I/Io @ 427 nm) of an indicator as described in Example 5.

The modulation of the fluorescence of the indicator macromolecule (which contains two recognition elements) prepared in this example by glucose, lactate and acetoacetate was determined. FIG. 4 shows the normalized fluorescence emission (I/Io @ 427 nm) of the hydrogel of this example in 10 mM PBS, pH 7.4 containing 0.2% $NaN_3$ and 1 mM EDTA containing various amounts of sodium-L-lactate, lithium acetoacetate or α-D-glucose. Data were recorded using a Shimadzu RF-5301 spectrofluorometer with excitation @365 nm (slit=3 nm) and emission at 427 nm (slit=3 nm) at low sensitivity at 37° C. using a temperature controlled sample holder. The cuvettes containing 3 mL of the desired solution were equilibrated at 37° C. for 15 minutes before measurement. Each hydrogel sample was measured in four independent samples. Error bars are standard deviation with quadruplicate values for each data point. The hydrogels containing a glucose recognition molecule were prepared as previously described. The hydrogels were mounted on glass slides and covered with polyester mesh in PMMA cuvettes at 45° to the incident light. Solutions of 1, 5, 10 and 20 mM sodium L-lactate [Aldrich], 5, 10 and 20 mM lithium acetoacetate [Aldrich], and 1, 2, 4, 5, 10, and 20 mM α-D-glucose were prepared in 10 mM PBS, pH 7.4 containing 0.2% $NaN_3$ and 1 mM EDTA. The fluorescence of the copolymer was affected by the presence of glucose, but not by the presence of lactate or acetoacetate.

EXAMPLE 6

Single- and Dual-Methacrylate Monomers of Bis-Boronate-Anthracene

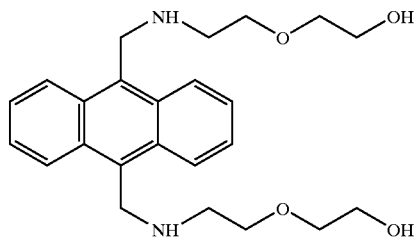

A. 9,10-bis[[2-(2-hydroxyethoxy)ethylamino]methyl]-anthracene.

To a solution of 2-(2-aminoethoxy)ethanol (31.4 g, 30.0 mL, 299 mmole, 20.9 equiv.) in 40 mL $CHCl_3$ at 23° C. was added 9,10-bis(chloromethyl)anthracene (3.94 g, 14.3 mmole). The solution was stirred in the dark for 67 hours. At this time, 100 mL $CH_2Cl_2$ were added and the solution was washed with 1×50 mL and 2×100 mL portions of $NaHCO_3$ (saturated aqueous solution). The organic extract was dried over anhydrous $Na_2SO_4$, filtered and concentrated to yield 4.67 g (79%) of a yellow powder. Product (~85% pure by RP-HPLC) was carried on as is.

HPLC conditions: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 15.6 min.

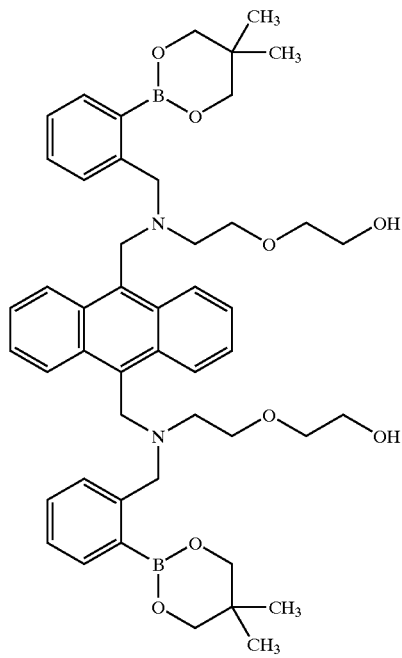

B. 9,10-bis[N-[2-(5,5-dimethyl-[1,3,2]dioxaborinan-2-yl) benzyl]-N-[2-(2-hydroxyethoxy) ethylamino]methyl] anthracene.

A solution of 9,10-bis[[2-(2-hydroxyethoxy)ethylamino]-methyl]anthracene (4.02 g, 9.75 mmole), DIEA (12.6 g, 17.0 mL, 97.5 mmole, 10.0 equiv.) and (2-bromomethylphenyl) boronic acid neopentyl ester (13.7 g, 48 mmole, 4.9 equiv.) in 125 mL $CHCl_3$ at 23° C. was stirred in the dark for 46 hours. At this time, the reaction mixture was concentrated initially by rotary evaporation, then using a vacuum pump to remove the DIEA. The residue was purified by alumina column chromatography (150 g activated neutral alumina, 0–3% $CH_3OH/CH_2Cl_2$) to yield 5.67 g (70%) of a viscous oil which solidified upon standing. Product (~85% pure by RP-HPLC) was carried on as is.

TLC: Merck basic alumina plates, Rf 0.33 with 95/5 $CH_2Cl_2/CH_3OH$, see with UV (254/366).

HPLC conditions: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 18.8 min.

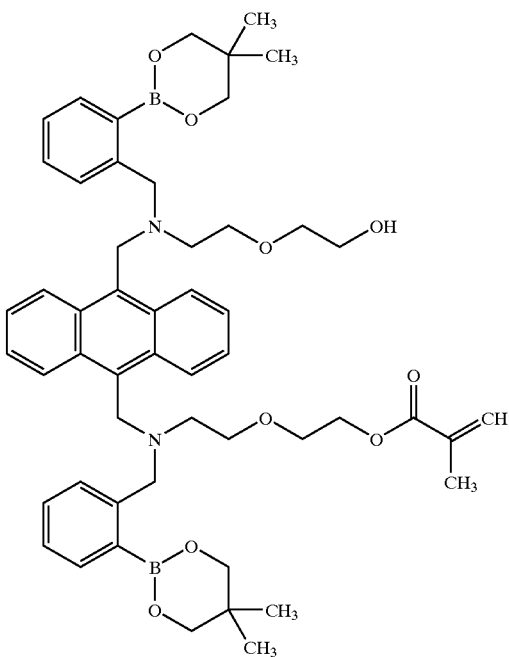

C. 9-[N-[2-(5,5-dimethyl-[1,3,2,]dioxaborinan-2-yl) benzyl]-N-[2-(2-methacroyloxyethoxy) ethylamino] methyl]-10-[N-[2-(5,5-dimethyl-[1,3,2,]dioxaborinan-2-yl) benzyl]-N-(2-(2-hydroxyethoxy)-ethylamino]methyl] anthracene. (Single-methacrylate monomer).

A solution of 9,10-bis[N-[2-(5,5-dimethyl-[1,3,2] dioxaborinan-2-yl)benzyl]-N-[2-(2-hydroxyethoxy)-ethylamino]methyl]-anthracene (0.298 g, 0.359 mmole), methacrylic acid (0.304 g, 0.300 mL, 3.53 mmole, 9.84 equiv.), DCC (0.965 g, 4.68 mmole, 13.0 equiv.) and N,N-dimethylamino-pyridine (0.020 g, 0.16 mmole, 0.46 equiv.) in 15 mL $CH_2Cl_2$ at 23° C. was stirred in the dark for 4 hours. At this time, the reaction mixture was filtered and concentrated by rotary evaporation. The residue was purified by alumina column chromatography (50 g activated neutral alumina, 0–4% $CH_3OH/CH_2Cl_2$) to yield 0.150 g (47%) of a yellow solid.

FAB MS: Calc'd for $C_{52}H_{66}B_2N_2O_9$ $[M]^+$ 885; Found $[M+1]^+$ 886.

TLC: Merck basic alumina plates, Rf 0.45 with 95/5 $CH_2Cl_2/CH_3OH$, see with UV (254/366).

HPLC: HP 1100 HPLC chromatograph, Vydac 201TP 10×250 mm column, 0.100 mL injection, 2 mL/min, 370 nm detection, A=water (0.1% HFBA) and B=MeCN (0.1% HFBA), gradient 10% B 2 min, 10–80% B over 18 min, 80–100% B over 2 min, 100% B 2 min, retention time 21 min.

D. Water soluble copolymer of 9-[N-[2-(5,5-dimethyl-[1,3,2]dioxaboriuian-2-yl)benzyl]-N-[2-(2-methacroyloxy-ethoxy) ethylamino]methyl]-10-[N-[2-(5,5-dimethyl-[1,3,2] dioxaborinan-2-yl)benzyl]-N-[2-(2-hydroxyethoxy) ethylamino]methyl]-anthracene and TMAXA(1:50 molar ratio).

To a solution of [2-(methacryloxy)ethyl]trimethyl-ammonium chloride (TMAMA, 70 wt % aqueous solution, 0.344 g monomer, 1.66 mmole, 50 equiv.) in 0.600 mL water was added a solution of 9-[N-[2-(5,5-dimethyl—[1,3,2,] dioxaborinan-2-yl) benzyl ]-N-[2-(2-methacroyloxyethoxy) ethylamino]-methyl]-10-[N-[2-(5,5-dimethyl-[1,3,2] dioxaborinan-2-yl)benzyl]-N-[2-(2-hydroxyethoxy) ethylamino]methyl]anthracene (0.029 g, 0.033 mmole) in 3.00 mL MeOH. To this mixture was added 4,4'-azobis (4-cyanovaleric acid) (0.0075 g, 0.027 mmole, 1.6 mole % of total monomer). The solution was filtered through a 0.45μ membrane filter, was purged with nitrogen gas and then heated in the dark at 55° C. for 16 hours. At this time, the viscous solution was cooled to 25° C. and concentrated in vacuo. The residue was diluted with 20 mL water and filtered through a 0.2 u membrane filter. The polymer solution was dialyzed through a cellulose acetate membrane (MWCO 3500) against 2×4 L of water. From the dialysis was obtained 38.5 mL of polymer solution. Concentration of a portion of this solution to dryness indicated 0.0075 g polymer per 1.0 mL solution. Overall 0.289 g (77%) yield of polymer.

E. Modulation of Fluorescence With Glucose, Lactate and Acetoacetate

Figure 5:
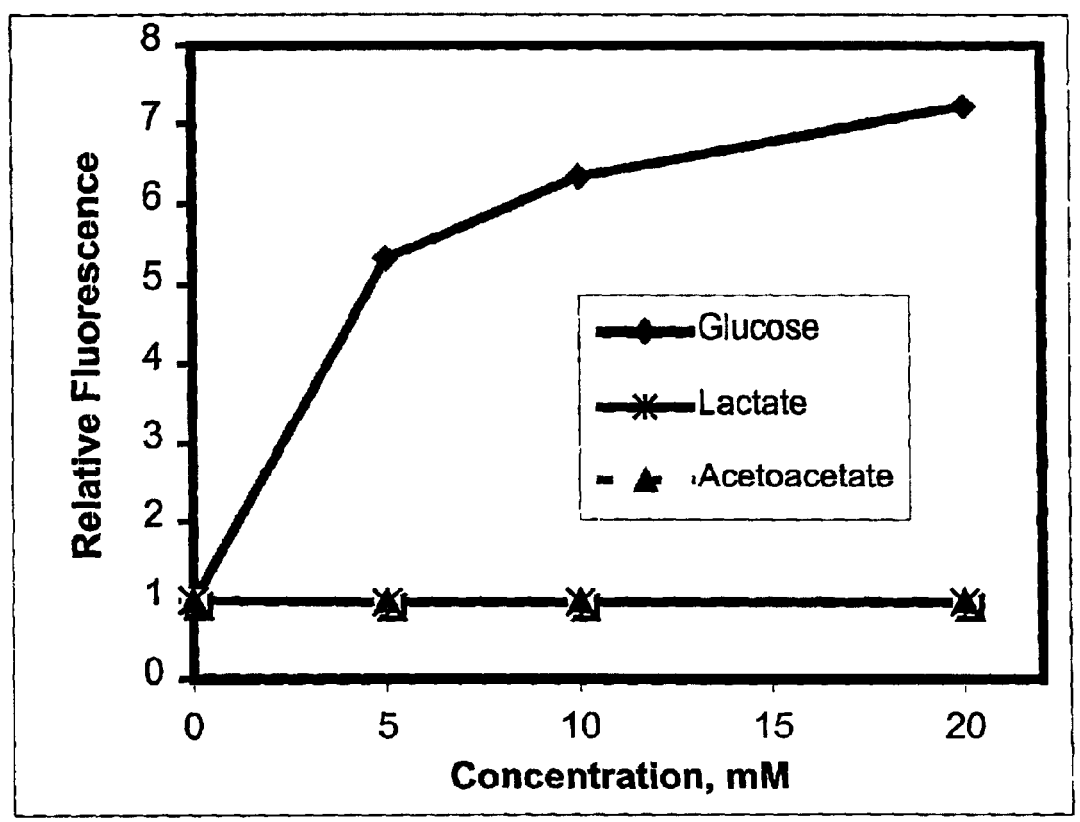
FIG. 5 illustrates the normalized fluorescence emission (I/Io @ 428 nm) of an indicator as described in Example 6.

The modulation of the fluorescence of the copolymer (which contains two recognition elements) prepared in step D of this example by glucose, lactate and acetoacetate was determined. FIG. 5 shows the normalized fluorescence emission (I/Io @ 428 nm) of a 1.5 mg/mL solution of anthracene bis boronate-TMAMA (1:50 mole ratio) copolymer in PBS containing a) 0–20 mM glucose; b) 0–20 mM lactate; c) 0–20 mM lithium acetoacetate. Spectra were recorded using a Shimadzu RF-5301 spectrafluorometer with excitation @365 nm; excitation slits at 1.5 nm; emission slits at 1.5 nm; ambient temperature. The fluorescence of the copolymer was affected by the presence of glucose, but not by the presence of lactate or acetoacetate.

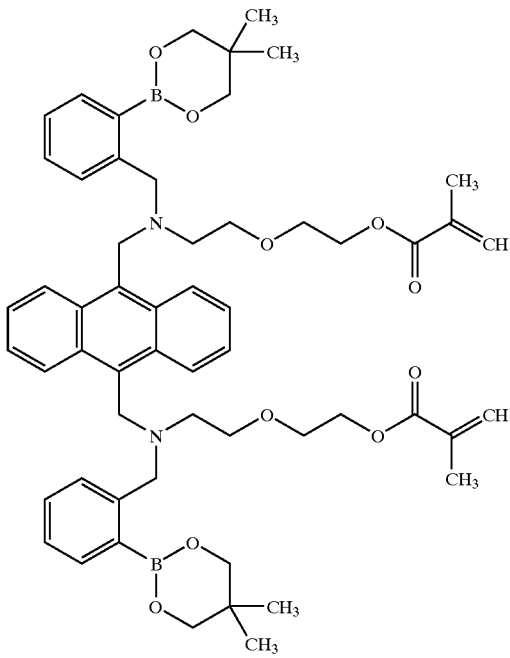

F. 9,10-bis [N-[2-(5,5-dimethyl-[1,3,2,]dioxaborinan-2-yl) benzyl]-N-[2-(2-methacroyloxyethoxy)ethylamino]-methyl]anthracene. (Dual-methacrylate monomer).

A solution of 9,10-bis[N-[2-(5,5-dimethyl-[1,3,2] dioxaborinan-2-yl)benzyl]N-[2-(2-hydroxyethoxy) ethylamino]methyl]-anthracene (0.100 g, 0.120 mmole), methacrylic acid (0.112 g, 0.110 mL, 1.30 mmole, 10.8 equiv.), DCC (0.316 g, 1.53 mmole, 12.8 equiv.) and N,N-dimethylamino-pyridine (0.014 g, 0.11 mmole, 0.92 equiv.) in 5 mL $CH_2Cl_2$ was stirred at 0° C. for 1 hour, then 23° C.

for 22 hours. At this time, the reaction mixture was filtered and concentrated by rotary evaporation. The residue was purified by alumina column chromatography (30 g activated neutral alumina, 0–2% $CH_3OH/CH_2Cl_2$) to yield 0.030 g (26%) of a yellow solid. This product may be copolymerized with one or more other monomers to form an indicator macromolecule. The boronate groups should be deprotected prior to use.

FAB MS: Calc'd for $C_{56}H_{70}B_2N_2O_{10}$ $[M]^+$ 953; Found $[M]^+$ 951 (weak molecular ion peak).

TLC: Merck basic alumina plates, Rf 0.67 with 95/5 $CH_2Cl_2/CH_3OH$, see with UV (254/366).

HPLC: HP 1100 HPLC chromatograph, Waters 5×100 mm NovaPak HR C18 column, 0.100 mL injection, 0.75 mL/min, 2 mL injection loop, 370 nm detection, A=water (0.1% HFBA) and B=MeCN (0.1% HFBA), gradient 10% B 2 min, 10–80% B over 18 min, 80–100% B over 2 min, 100% B 2 min, retention time 19.6 min.

G. Preparation of HEMA/SPE/MAA Hydrogel with Glucose Indicator:

A solution of hydroxyethyl methacrylate (HEMA, 0.078 mL, 0.084 g, 0.64 mmol), methacrylic acid (MAA, 0.030 mL, 0.030 g, 0.35 mmol), polyethyleneglycol dimethacrylate 1000 (PEGDMA, 0.5 mg/mL aqueous solution, 0.048 mL), and N,N-dimethyl-N-methacryloxyethyl-N-(3-sulfopropyl)-ammonium-batain (SPE, 0.462 g, 1.65 mmol) in 0.900 mL of ethylene glycol was prepared. 9,10-bis[N-[2-(5,5-dimethyl-[1,3,2,]dioxaborinan-2-yl)benzyl)-N-[2-(2-methacroyloxyethoxy) ethylamino]-methyl]anthracene (0.0096 g, 0.010 mmol) and 0.020 mL of 5% wt. aqueous solution of ammonium persulfate were combined with 0.500 mL of the ethylene glycol monomer solution. This solution was placed in glove box purged with nitrogen. An aqueous solution of N,N,N',N'-tetramethylethylenediamine (0.040 mL, 5% wt.) was added to the monomer formulation to accelerate polymerization. The resulting formulation was poured in a mold constructed from microscope slides and a 100 micron stainless steel spacer. After being kept for 8 hours in nitrogen atmosphere the mold was placed in phosphate buffered saline (PBS, pH=7.4), the microscope slides were separated, and the hydrogel was removed. The hydrogel was washed with 100 mL of PBS containing 1 mM lauryl sulfate sodium salt for 3 days, the solution being changed every day, followed by washing with MeOH/PBS (20/80 by vol. 3×100 mL), and finally with PBS (3×100 ML). The resulting hydrogel polymer was stored in PBS (pH=7.4) containing 0.2% wt. sodium azide and 1 mM EDTA sodium salt.

Figure 6:
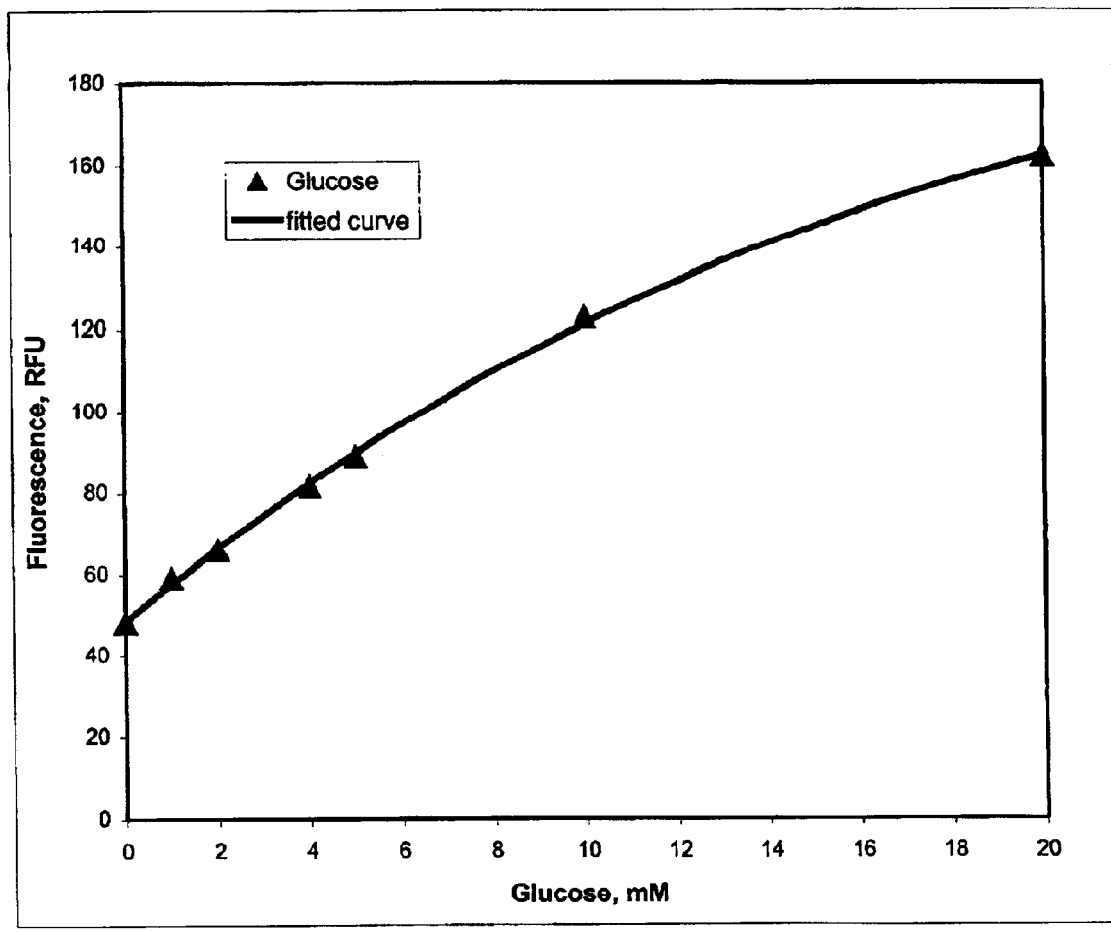
FIG. 6 illustrates the normalized fluorescence emission (I/Io @ 427 nm) of an indicator as described in Example 6.

H. Modulation of Fluorescence with Glucose:

The modulation of the fluorescence of the dual methacrylate indicator compound prepared in this example by glucose was determined. FIG. 6 shows the relative fluorescence emission (I@427 nm) of a HEMA/SPE hydrogel (100 micron thickness, prepared as previously described) containing the dual methacrylate glucose recognition molecule of this example in PBS (pH 7.4 containing 0.2% $NaN_3$ and I mM EDTA) containing 0 to 20 mM α-D-glucose. The hydrogels were mounted on glass slides and covered with black polyester mesh (so far America, Depew, N.Y.) in PMMA cuvettes at 45° to the incident light. All measurements were made at 37° C. in a Shimadzu RF-5301 spectrofluorometer with excitation at 365 nm (slit=1.5 nm) and emission at 427 nm (slit=1.5 nm) at high sensitivity using a temperature controlled sample holder. The cuvettes containing 3 mL of the desired glucose solution (0, 1, 2, 4, 5, 10, 20 mM glucose) were equilibrated at 37 C for 30 minutes before measurement. A single exponential function was used to fit the raw fluorescence data.

EXAMPLE 7

Effect of glucose or lactate on acrylamide gel containing N-[3-(methacrylamido)propyl]-3,4-dihydroxy-9,10-dioxo-2-anthracenesulfonamide (Alizarin Red S monomer) and α,α'-bis [N-[2-(5,5-dimethyl-[1,3,2,]dioxaborinan-2-yl) benzyl]-N-[3-(methacrylamido) propylamino]-1,4-zylene (bis boronic acid monomer):

A. 3,4-Dihydroxy-9,10-dioxo-2-anthracenesulfonyl chloride:

3,4-dihydroxy-9,10-dioxo-2-anthracenesulfonic acid sodium salt (1.4 g, 3.9 mmoles) was combined with 30 mL of chlorosulfonic acid and heated to 90° C. for 5 hours, after which the solution was cooled to 0° C. and poured into 100 g of ice. After the ice melted the solution was extracted with $CH_2Cl_2$ (3×100 mL), methylene chloride extracts were combined, dried with $Na_2SO_4$ and evaporated to produce 0.87 g of solid (Yield 66%).

B. N-[3-(methacrylamido)propyl]-3,4-dihydroxy-9,10-dioxo-2-anthracenesulfonamide:

3,4-dihydroxy-9,10-dioxo-2-anthracenesulfonyl chloride (96 mg, 0.28 mmoles) and N-(3-aminopropyl) methacrylamide hydrochloride (108 mg, 0.6 mmoles) were combined with 20 mL of $CH_2Cl_2$. To this suspension $Et_3N$ (303 mg, 3 mmoles) was added. The mixture was stirred at room temperature for 24 hours, filtered, and solvent was evaporated. The resulting solid was subjected to column chomatography on $SiO_2$ (10 g) with $CH_2Cl_2$/MeOH (90/10) as an eluent. The product was obtained as a red solid (80 mg, 64% yield).

FAB MS: Calculated for $C_{21}H_{20}N_2O_7S$ $M^+$ 445; Found $M^+$ 445.

HPLC: HP 1100 HPLC chromatograph, Waters 5×100 mm NovaPak HR C18 column, 0.100 mL injection, 0.75 mL/min, 2 mL injection loop, 370 nm detection, A=water (0.1% HFBA) and B=MeCN (0.1% HFBA), gradient 10% B 2 min, 10–80% B over 18 min, 80–100% B over 2 min, 100% B 2 min, retention time 17.67 min.

C. α,α'-bis[3-(methacrylamido)propylamino]-1,4-xylene.

A solution of N-(3-aminopropyl)methacrylamide hydrochloride salt (3.00 g, 16.8 mmole, 2.21 equiv.), DIEA (6.5 g, 8.8 mL, 50 mmole, 6.6 equiv.), terephthaldicarboxaldehyde (1.02 g, 7.60 mmole) and $Na_2SO_4$ (10.7 g, 75.3 mmole, 9.91 equiv.) in 75 mL anhydrous MeOH was stirred in the dark at 25° C. for 18 hours. At this time, more $Na_2SO_4$ (10.7 g, 75.3 mmole, 9.91 equiv.) was added and stirring continued for 6 hours longer. At this time, the solution was filtered and $NaBH_4$ (1.73 g, 45.7 mmole, 6.01 equiv.) was added to the filtrate in portions and subsequently stirred at 25° C. for 21 hours. The suspension was filtered through Celite and the filtrate was concentrated. The residue was dissolved in 100 mL $CH_2Cl_2$ and washed 1×25 mL saturated aqueous $NaHCO_3$. The organic extract was dried over anhydrous $Na_2SO_4$, filtered and concentrated to yield a viscous oil. The product was carried on as is.

HPLC: HP 1100 HPLC chromatograph, Vydac 201TP 10×250 mm column, 0.100 mL injection, 2.00 mL/min, 260 nm detection, A=water (0.1% HFBA) and B=MeCN (0.1% HFBA), gradient 10% B 2 min, 10–80% B over 18 min, 80–100% B over 2 min, 100% B 2 min, retention time 15.8 min.

D. α,α'-bis[N-(2-(5,5-dimethyl-[1,3,2,]dioxaborinan-2-yl)-benzyl]-N-[3-(methacrylamido)propylamino]-1,4-xylene.

A solution of α,α'-bis[3-(methacrylamido)-propylamino]-1,4-xylene (2.94 g, 7.61 mmole), DIEA (2.97 g, 4.00 mL, 23.0 mmoles, 3.02 equiv.), (2-bromomethyl-phenyl)boronic acid neopentyl ester (6.50 g, 23.0 mmole, 3.02 equiv.) and BHT (5 mg as inhibitor) in 75 mL $CH_2Cl_2$ at 25° C. was stirred in the dark for 28 hours. At this time, the mixture was washed 1×25 mL saturated aqueous $NaHCO_3$. The organic extract was dried over anhydrous $Na_2SO_4$, filtered and concentrated. To the residue was added 200 mL ether and the suspension was stirred for 18 hours. The suspension was filtered and the residue dissolved in $CH_2Cl_2$, filtered and the filtrate concentrated. To the solid residue was added 150 mL ether and the suspension was stirred for 18 hours. At this time, the suspension was filtered yielding 1.98 g (33%) of a fluffy pink powder, which had a maximum solubility of 1 mmolar in PBS (pH 7.4).

FAB MS: Calc'd for $C_{46}H_{64}B_2N_4O_6$ $[M]^+$ 790; Found $[M+1]^+$ 791.

HPLC: HP 1100 HPLC chromatograph, Waters 5×100 mm NovaPak HR C18 column, 0.050 mL injection, 0.75 mL/min, 280 nm detection, A=water (0.1% HFBA) and B=MeCN (0.1% HFBA), gradient 10% B 2 min, 10–80% B over 18 min, 80–100% B over 2 min, 100% B 2 min, retention time 13.4 min.

E. Preparation of acrylamide gel containing N-[3-(methacrylamido)propyl]-3,4-dihydroxy-9, 10-dioxo-2-anthracenesulfonamide (Alizarin Red S monomer) and α,α'-bis [N-[2-(5,5-dimethyl-[1,3,2,]dioxaborinan-2-yl) benzyl]-N-(3-(methacrylamido)propylaminoj-1,4-xylene:

Ethylene glycol solution containing 30% wt. acrylamide and 0.8% wt. N,N'-methylenebisacrylamide was prepared. N-[3-(methacrylamido)propyl]-3,4-dihydroxy-9, 10-dioxo-2-anthracenesulfonamide (1.5 mg, $3.38×10^{-6}$ mole) and α,α'-bis[N-[2-(5,5-dimethyl-[1,3,2,]dioxaborinan-2-yl)benzyl]-N-(3-(methacrylamido)propylamino]-1, 4-xylene (28 mg, $3.54 ×10^{-5}$ mole) were combined with 800 μL of ethylene glycol monomer solution and 40 μL of 5% wt. aqueous ammnonium persulfate. This formulation was placed in a glove box purged with nitrogen along with a mold constructed from glass microscope slides and 100 micron stainless steel spacer. An aqueous solution of N,N,N',N'-tetramethylethylenediamine (40 μL, 5% wt.) was added to the monomer solution to accelerate polymerization and the final formulation was poured into a glass mold. The mold was left under nitrogen atmosphere for 16 hours, after which it was immersed in PBS (pH=7.4) and the glass slides were separated to afford a hydrogel polymer in a form of a thin film. The resulting hydrogel thin film was washed with 100 mL of phosphate buffered saline containing 1 mM lauryl sulfate sodium salt for 3 days, the solution being changed every day, followed by washing with MeOH/PBS (20/80 by vol., 3×100 mL), and finally with PBS (pH=7.4, 3×100 mL). Hydrogel polymer was stored in PBS (10 mM PBS, pH=7.4) containing 0.2% wt. sodium azide and 1 mM EDTA sodium salt.

F. Modulation of Absorbance With Glucose and Lactate

The modulation of the absorbance of the indicator hydrogel (which contains two recognition elements) prepared in this example by glucose and lactate was determined. The acrylamide gel was mounted in PMMA cell in the same way as described in Example 5. Phosphate buffered saline (PBS), pH=7.4 containing the desired amount of glucose or sodium lactate was heated to 37° C. in a water bath and placed in the PMMA cell containing the gel after which the PMMA cell was allowed to equilibrate for 15 min at 37° C. Absorbance measurement for each glucose or lactate concentration was conducted in triplicate. For each measurement, absorbance at 650 nm was used as a blank, A(650 nm) was subtracted from all values of A(450 nm) and A(530 nm).

Figure 7:
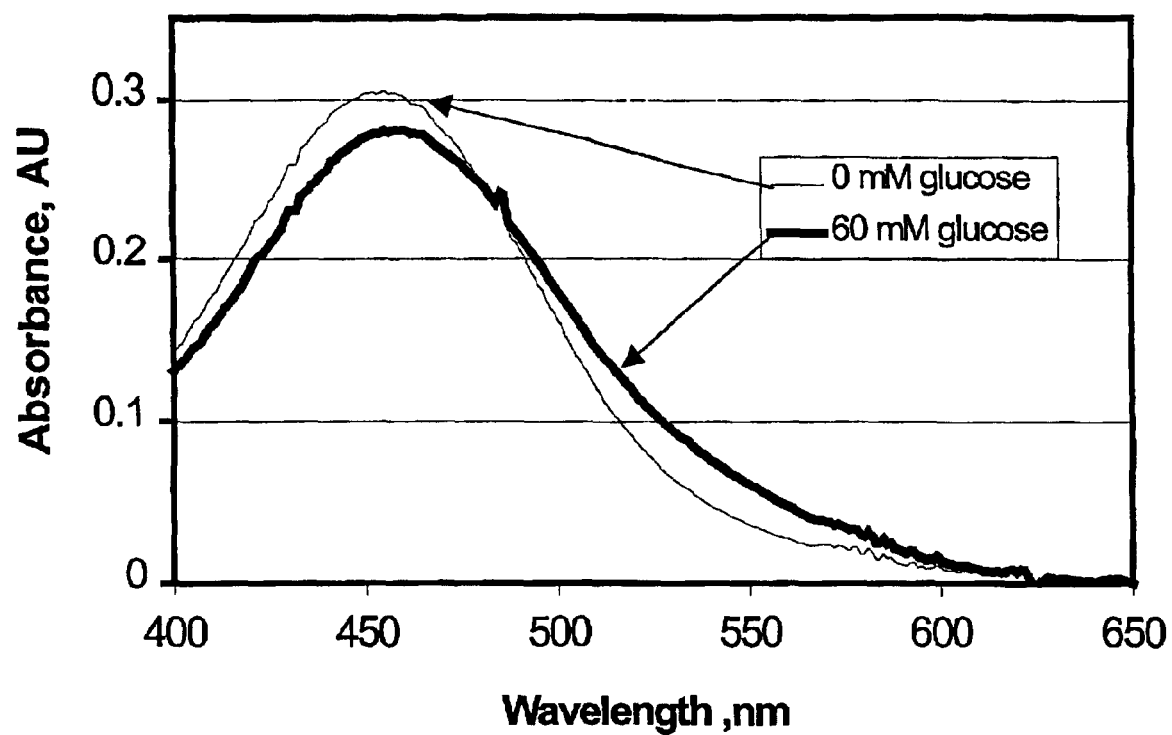
FIG. 7 illustrates the absorbance spectra of an indicator as described in Example 7.
Figure 8:
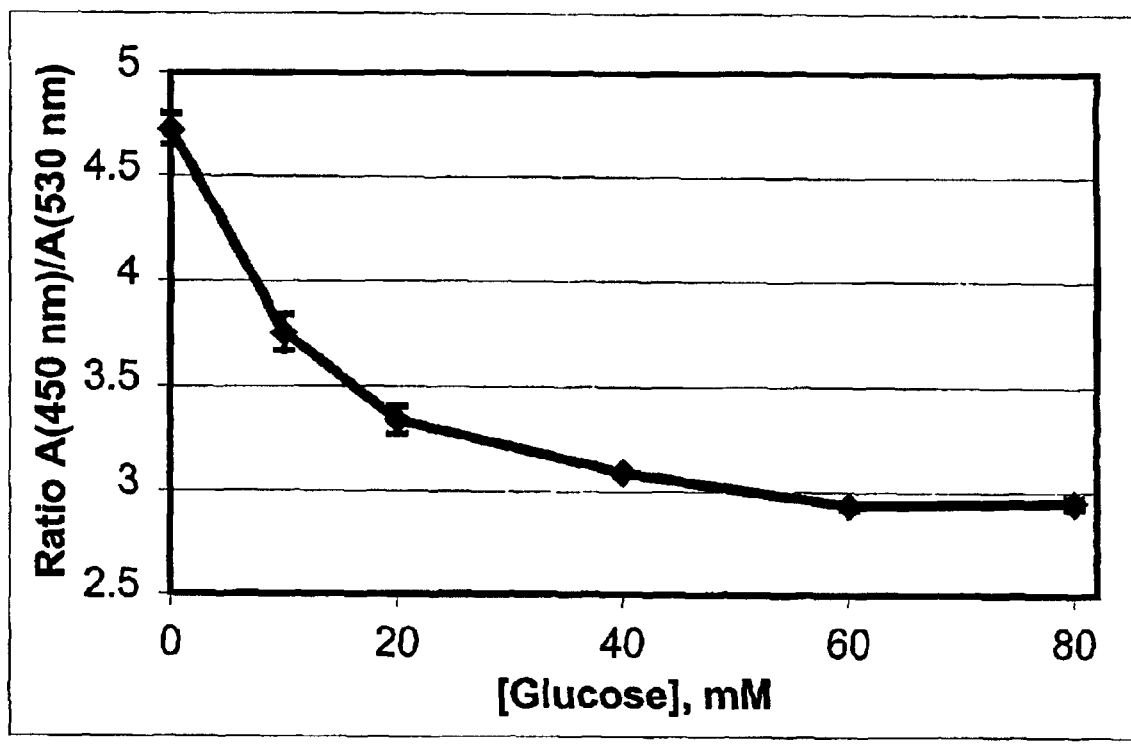
FIGS. 8–9 illustrate the ratio of the absorbance (450 nm/530 nm) of an indicator as described in Example 7.
Figure 9:
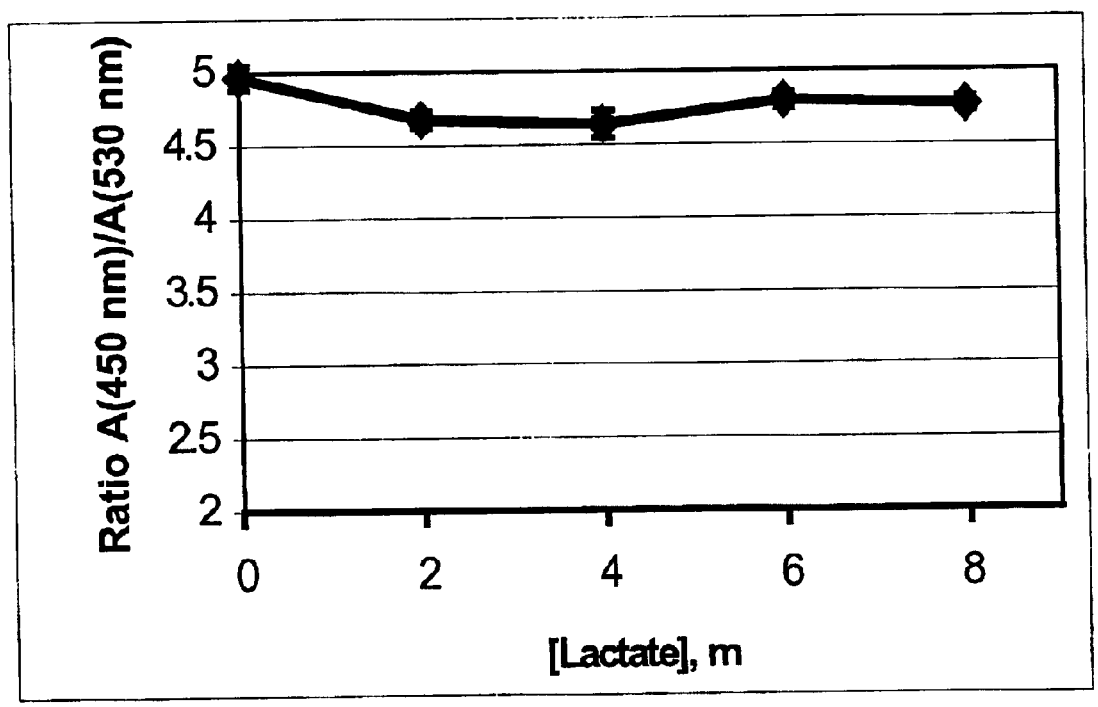

FIG. 7 shows the absorbance spectra for acrylamide gel (30%) containing 4 mM Alizarin Red S monomer (1:1000 molar ratio of Alizarin Red:acrylamide) and 44 mM bis boronic acid monomer (1:95 molar ratio of boronic acid monomer:acrylamide) with and without glucose. FIG. 8 shows the effect of glucose on absorbance of acrylamide gel (30%) containing 4 mM Alizarin Red S monomer and 44 mM bis boronic acid monomer. FIG. 9 shows the effect of sodium lactate on absorbance of acrylamide gel (30%) containing 4 mM Alizarin Red S monomer and 44 mM bis boronic acid monomer. The absorbance of the indicator was affected by the presence of glucose, but not substantially affected by the presence of lactate.

What is claimed is:

1. An indicator macromolecule for detecting the presence or concentration of an analyte in an aqueous environment, said macromolecule comprising a copolymer of:
    a) one or more indicator component monomers which individually are not sufficiently water soluble to permit their use in an aqueous environment for detecting the presence or concentration of said analyte; and
    b) one or more hydrophilic monomers; such that the macromolecule is capable of detecting the presence or concentration of said analyte in an aqueous environment.

2. The indicator macromolecule of claim 1, wherein the macromolecule is capable of detection by an optical change.

3. The indicator macromolecule of claim 1, wherein the indicator component monomer comprises an N-(o-boronobenzyl) aminomethylanthracene derivative.

4. The indicator macromolecule of claim 3, wherein the indicator component monomer is selected from the group consisting of 9-[[N-methacryloylaminopropyl-N-(o-boronobenzyl) amino]-methyl]anthracene;

9-[N-[2-(5,5-dimethyl-[1,3,2]dioxaborinan-2-yl)benzyl]-N-[3-(methacrylamido) propylamino]methyl]-10-[N-[2-(5,5-dimethyl-[1,3,2]dioxaborinan -2-yl)benzyl]-N-[2-(2-hydroxyethoxy)-ethylamino ]methyl]anthracene;

9-[N-(2-boronobenzyl)-N-[3-(methacrylamido)-propylaminolmethyl]-10-(N-(2-boronobenzyl)-N-[2-(2-hydroxyethoxy) ethylamino]methyl]anthracene;

9,10-bis [N-[2-(5,5-dimethyl-[1,3,2]dioxaborinan-2-yl) benzyl]-N-[3-(methacrylamido) propylaminolmethyl] anthracene;

9,10-bis [N-(2-boronobenzyl)-N-[3-(methacrylamido)-propylamino]methyl]anthracene;

9-N-[2-(5,5-dimethyl-[1,3,2]dioxaborinan-2-yl)benzyl]-N-[2-(2-methacroyloxyethoxy) ethylamino]methyl]-10-[N-[2-(5,5-dimethyl-[1,3,2]dioxaborinan-2-yl) benzyl]-N-[2-(2-hydroxyethoxy)-ethylamino ]methyl] anthracene;

9-[N-(2-boronobenzyl)-N-[2-(2-methacroyloxyethoxy)-ethylamino]methyl]-10-[N-[2-boronobenzyl)]-N-[2-(2-hydroxyethoxy) ethylamino]methyl]anthracene;

9, 10-bis (N-[2-(5, 5-dimethyl-[1,3,2]dioxaborinan-2-yl) benzyl]-N-[2-(2-methacroyloxyethoxy) ethylamino] methyl]anthracene;

9, 10-bis [N-(2-boronobenzyl)-N-[2-(2-methacroyloxyethoxy) ethylamino]methyl]anthracene; and salts or derivatives thereof.

5. The indicator macromolecule of claim 3, wherein the hydrophilic monomer comprises [3-(methacryloylamino)-propyl]trimethylammonium chloride.

6. The indicator macromolecule of claim 1, wherein the indicator component monomer is selected from the group consisting of a lanthanide chelate and a polyaromatic hydrocarbon.

7. The indicator macromolecule of claim 1, wherein the molar ratio of hydrophilic monomer:indicator component momomer is from about 2:1 to about 1000:1.

8. The indicator macromolecule of claim 7, wherein the ratio of hydrophilic monomer:indicator component momomer is from about 5:1 to about 50:1.

9. The indicator macromolecule of claim 8, wherein the ratio of hydrophilic monomer:indicator component momomer is about 5:1.

10. The indicator macromolecule of claim 1, wherein the analyte detected is selected from the group consisting of a vicinal diol; an α-hydroxy acid, a β-keto acid oxygen; carbon dioxide; zinc, potassium, hydrogen, or carbonate ions; a toxin; a mineral; and a hormone.

11. The indicator macromolecule of claim 10, wherein the analyte detected is a vicinal diol which comprises a saccharide.

12. The indicator macromolecule of claim 11, wherein the saccharide is glucose.

13. The indicator macromolecule of claim 1, wherein
    i) the molar ratio of hydrophilic monomer:indicator component momomer is from about 2:1 to about 15:1,
    ii) the indicator component monomer comprises an N-(o-boronobenzyl) amino]methyl]anthracene derivative,
    iii) the hydrophilic monomer comprises [3-(methacryloylamino) propyl]trimethylammonium chloride, and
    iv) the macromolecule exhibits an excimer effect.

14. The indicator macromolecule of claim 1, wherein the indicator component monomer is selected from the group consisting of:
    N-[3-(methacrylamido)propyl]-3,4-dihydroxy-9,10-dioxo-2-anthracenesulfonamide; α,α'-bis [N-[2-(5,5-dimethyl-[1,3,2]dioxaborinan-2-yl) benzyl]-N-[3-(methacrylamido)propylamino]-1, 4-xylene; and salts or derivatives thereof.

15. A method for the production of an indicator macromolecule for detecting the presence or concentration of an analyte in an aqueous environment, said method comprising copolymerizing:
    a) one or more indicator component monomers which individually are not sufficiently water soluble to permit their use in an aqueous environment for detecting the presence or concentration of said analyte; and
    b) one or more hydrophilic monomers; such that the resulting macromolecule is capable of detecting the presence or concentration of said analyte in an aqueous environment.

16. The method of claim 15, wherein the macromolecule is capable of detection by an optical change.

17. The method of claim 15, wherein the indicator component monomer comprises an N-(o-boronobenzyl) aminomethylanthracene derivative.

18. The method of claim 17, wherein the indicator component monomer is selected from the group consisting of
    9-[[N-methacryloylaminopropyl-N-(o-boronobenzyl) amino]-methyl]anthracene;
    9-[N-[2-(5,5-dimethyl-[1,3,2]dioxaborinan-2-yl)benzyl]-N-[3-(methacrylamido) propylamino]methyl]-10-[N-[2-(5,5-dimethyl-[1,3,2]dioxaborinan-2-yl) benzyl]-N-[2-(2-hydroxyethoxy)-ethyl amino]methyl]anthracene;
    9-[N-(2-boronobenzyl)-N-[3-(methacrylamido)-propylamino]methyl]-10-[N-(2-boronobenzyl)-N-[2-(2-hydroxyethoxy) ethylamino]methyl]anthracene;
    9,10-bis[N-[2-(5,5-dimethyl-[1, 3, 2]dioxaborinan-2-yl) benzyl]-N-[3-(*methacrylamido)propylamino]methyl] anthracene;
    9, 10-bis [N-(2-boronobenzyl)-N-[3-(methacrylamido)-propylamino]methyl]anthracene;
    9-[N-[2-(5, 5-dimethyl-[1,3,2]dioxaborinan-2-yl)benzyl]-N-[2-(2-methacroyloxyethoxy) ethylamino]methyl]-10-[N-[2-(5,5-dimethyl-[1,3,2]dioxaborinan-2-yl) benzyl]-N-[2-(2-hydroxyethoxy)-ethylamino]methyl] anthracene;
    9-[N-(2-boronobenzyl)-N-[2-(2-methacroyloxyethoxy)-ethylamino]methyl]-10-[N-[2-boronobenzyl)]-N-[2-(2-hydroxyethoxy) ethylamino]methyl]anthracene;
    9,10-bis [N-[2-(5,5-dimethyl-[1,3,2dioxaborinan-2-yl) benzyl]-N-[2-(2-methacroyloxyethoxy) ethylamino] methyl]anthracene;
    9,10-bis [N-(2-boronobenzyl)-N-[2-(2-methacroyloxyethoxy) ethylamino]methyl) anthracene; and salts or derivatives thereof.

19. The method of claim 15, wherein the hydrophilic monomer comprises [3-(methacryloylamino)-propyl]trimethylammonium chloride.

20. The method of claim 15, wherein the indicator component monomer is selected from the group consisting of a lanthanide chelate and a polyaromatic hydrocarbon.

21. The method of claim 15, wherein the molar ratio of hydrophilic monomer:indicator component momomer is from about 2:1 to about 1000:1.

22. The method of claim 21, wherein the ratio of hydrophilic monomer:indicator component momomer is from about 5:1 to about 50:1.

23. The method of claim 22, wherein the ratio of hydrophilic monomer:indicator component momomer is about 5:1.

24. The method of claim 15, wherein the analyte detected is selected from the group consisting of a vicinal diol; an α-hydroxy acid; a β-keto acid; oxygen; carbon dioxide; zinc, potassium, hydrogen, or carbonate ions; a toxin; a mineral; and a hormone.

25. The method of claim 24, wherein the analyte detected is a vicinal diol which comprises a saccharide.

26. The method of claim 25, wherein the saccharide is glucose.

27. The method of claim 15, wherein
    i) the molar ratio of hydrophilic monomer:indicator component momomer is from about 2:1 to about 15:1,
    ii) the indicator component monomer comprises an N-(o-boronobenzyl) aminomethylanthracene derivative,
    iii) the hydrophilic monomer comprises [3-(methacryloylamino) propyl]trimethylammonium chloride, and
    iv) the macromolecule exhibits an excimer effect.

28. The method of claim 15, wherein the indicator component monomer is selected from the group consisting of:
    N-[3-(methacrylamido) propyl]-3, 4-dihydroxy-9, 10-dioxo-2-anthracenesulfonamide;
    α,α-bis-(2-(5, 5-dimethyl-[1,3,2°dioxaborinan-2-yl) benzyl[-N-[3-(methacrylamido)propylamino]-1, 4-xylene; and salts or derivatives thereof.

29. A method for detecting the presence or concentration of an analyte in a sample having an aqueous environment, said method comprising:
    a) exposing the sample to an indicator macromolecule, said macromolecule comprising a copolymer of:
        i) one or more indicator component monomers which individually are not sufficiently water soluble to permit their use in an aqueous environment for detecting the presence or concentration of said analyte; and ii) one or more hydrophilic monomers; such that the resulting macromolecule is capable of detecting the presence or concentration of said analyte in an aqueous environment, and wherein the indicator macromolecule has a detectable quality that changes in a concentration-dependent manner when said macromolecule is exposed to said analyte; and b) measuring any change in said detectable quality to thereby determine the presence or concentration of said analyte in said sample.

30. The method of claim 29, wherein the change in said detectable quality is an optical change.

31. The method of claim 29, wherein the indicator component monomer comprises an N-(o-boronobenzyl) aminomethylanthracene derivative.

32. The method of claim 31, wherein the indicator component monomer is selected from the group consisting of 9-[[N-methacryloylaminopropyl-N-(o-boronobenzyl) amino]-methyl]anthracene;

9-[N-[2-(5,5-dimethyl-[1,3,2]dioxaborinan-2-yl)benzyl]-N-[3-(methacrylamido) propylamino]methyl]-10-[N-[2-(5,5-dimethyl-[1,3,2]dioxaborinan-2-yl)benzyl]-N-[2-(2-hydroxyethoxy)-ethylamino]methyl]anthracene;

9-[N-(2-boronobenzyl)-N-[3-(methacrylamido)-propylamino]methyl]-10-[N-(2-boronobenzyl)-N-[2-(2-hydroxyethoxy) ethylamino]methyl]anthracene;

9,10-bis [N-(2-(5,5-dimethyl-[1,3,2dioxaborinan-2-yl) benzyl]-N-[3-(methacrylamido) propyl amino]methyl] anthracene;

9,10-bis [N-(2-boronobenzyl)-N-[3-(methacrylamido)-propyl amino]methyl anthracene;

9-[N-[2-(5,5-dimethyl-[1,3,2]dioxaborinan-2-yl)benzyl]-N-[2-(2-methacroyloxyethoxy) ethylamino]methyl]-10-[N-[2-(5,5-dimethyl-[1, 3,2]dioxaborinan-2-yl) benzyl]-N-[2-(2-hydroxyethoxy)-ethyl amino]methyl] anthracene;

9-[N-(2-boronobenzyl)-N-[2-(2-methacroyloxyethoxy)-ethylamino]methyl]-10-[N-[2-boronobenzyl)]-N-[2-(2-hydroxyethoxy) ethylamino]methyl]anthracene;

9,10-bis [N-[2-(5,5-dimethyl-[1,3,2]dioxaborinan-2-yl) benzyl]-N-[2-(2-methacroyloxyethoxy) ethylamino] methyl]anthracene;

9,10-bis [N-(2-boronobenzyl)-N-(2-(2-methacroyloxyethoxy) ethylamino]methyl]anthracene; and salts or derivatives thereof.

33. The method of claim 29, wherein the hydrophilic monomer comprises [3-(methacryloylamino)-propyl] trimethylammonium chloride.

34. The method of claim 29, wherein the indicator component monomer is selected from the group consisting of a lanthanide chelate and a polyaromatic hydrocarbon.

35. The method of claim 29 wherein the molar ratio of hydrophilic monomer:indicator component momomer is from about 2:2 to about 1000:1.

36. The method of claim 35, wherein the ratio of hydrophilic monomer:indicator component momomer is from about 5:1 to about 50:1.

37. The method of claim 36 wherein the ratio of hydrophilic monomer:indicator component momomer is about 5:1.

38. The method of claim 29, wherein the analyte detected is selected from the group consisting of a vicinal diol: an α-hydroxy acid: a β-keto acid: oxygen; carbon dioxide; zinc; potassium, hydrogen, or carbonate ions; a toxin; a mineral; and a hormone.

39. The method of claim 38, wherein the analyte detected is a vicinal did which comprises a saccharide.

40. The method of claim 39, wherein the saccharide is glucose.

41. The method of claim 29, wherein i) the molar ratio of hydrophilic monomer:indicator component momomer is from about 2:1 to about 15:1, ii) the indicator component monomer comprises an N-(o-boronobenzyl) aminomethylarithracene derivative, iii) the hydrophilic monomer comprises [3-(methacryloylamino) propyl]trimethylammonium chloride, and iv) the macromolecule exhibits an excimer effect.

42. The method of claim 41, wherein said macromolecule serves as both an indicator and a reference.

43. The method of claim 29, wherein the indicator component monomer is selected from the group consisting of:

N-[3-(methacrylamido)propyl]-3,4-dihydroxy-9,10-dioxo-2-anthracenesulfonamide;

α,α'-bis[N-[2-(5,5-dimethyl-[1,3,2]dioxaborinan-2-yl) benzyl]-N-[3-(methacrylamido) propylamino]-1, 4-xylene; and salts or derivatives thereof.

44. A macromolecule which is capable of exhibiting an excimer effect, which comprises a copolymer of:

a) one or more excimer forming monomers, the molecules of which are capable of exhibiting an excimer effect when suitably oriented with respect to each other; and b) one or more other monomers; such that the resulting macromolecule exhibits said excimer effect.

45. The macromolecule of claim 44, wherein the macromolecule is capable of detecting the presence or concentration of an analyte.

46. The macromolecule of claim 45, wherein a) the excimer forming monomer individually is not sufficiently water soluble to permit its use in an aqueous environment for detecting the presence or concentration of said analyte; and b) the other monomer is a hydrophilic monomer; such that the macromolecule is capable of detecting the presence or concentration of said analyte in an aqueous environment.

47. The macromolecule of claim 45, wherein the excimer effect does not substantially change in response to changes in the presence or concentration of the analyte.

48. The macromolecule of claim 47, wherein i) the molar ratio of other monomer:excimer forming momomer is from about 2:1 to about 15:1, ii) the excimer forming monomer comprises an N-(o-boronobenzyl) aminomethylanthracene derivative, and iii) the other monomer comprises [3-(methacryloylamino) propyl]trimethylammonium chloride.

49. The macromolecule of claim 44, wherein the excimer forming monomer is selected from the group consisting of a lanthanide chelate and a polyaromatic hydrocarbon.

50. The macromolecule of claim 48, wherein the excimer forming monomer is selected from the group consisting of 9-[[N-methacryloylaminopropyl-N-(o-boronobenzyl) amino]-methyl]anthracene;

9-[N-[2-(5,5-dimethyl-[1,3,2]dioxaborinan-2-yl)benzyl]-N-[3-(methacrylamido) propylamino]methyl]-10-[N-[2-(5, 5-dimethyl[1,3,2]dioxaborinan-2-yl)benzyl]-N-[2-(2-hydroxyethoxy)-ethylamino]methyl]anthracene;

9-[N-(2-boronobenzyl)-N-]3-(methacrylamido)-propylaminolmethyl]-10-[N-(2-boronbenzyl)-N-[2-(2-hydroxyethoxy) ethylamino]methyl]anthracene;

9,10-bis[N-[2-(5,5-dimethyl-[1,3,2]dioxaborinan-2-yl) benzyl]-N-(3-(methacrylamido) propylamino]methyl] anthracene;

9, 10-bis [N-(2-boronobenzyl)-N-[3-(methacrylamido)-propylamino]methylanthracene;

9-[N-[2-(5,5-dimethyl-[1,3,2]dioxaborinan-2-yl)benzyl]-N-[2]-(2-methacroyloxyethoxy) ethylamino]methyl]-10-[N-[2-(5,5-dimethyl-[1,3,2]dioxaborinan-2-yl) benzyl]-N-[2-(2-hydroxyethoxy)-ethylamino]methyl] anthracene;

9-[N-(2-boronobenzyl)-N-[2-(2-methacroyloxyethoxy)-ethylamino]methyl]-10-[N-(2-boronobenzyl)-N-[2-(2-hydroxyethoxy) ethylamino]methyl]anthracene;

9,10-bis[N-[2-(5,5-dimethyl-[1,3,2]dioxaborinan-2-yl) benzyl]-N-(2-(2-methacroyloxyethoxy) ethylamino] methyl]anthracene;

9,10-bis [N-(2-boronobenzyl)-N-[2-(2-methacroyloxyethoxy) ethylamino]methyl]anthracene; and salts or derivatives thereof.

51. The macromolecule of claim 44, wherein the excimer forming monomer is selected from the group consisting of:

N-[3-(methacrylamido)propyl]-3,4-dihydroxy-9,10-dioxo-2-anthracenesulfonamide;

α,α'-bis[N-]2-(5,5-dimethyl-[1,3,2]dioxaborinan-2-yl) enzyl]-N-[3-(methacrylamido)propylamino]-1,4-xylene; and salts or derivatives thereof.

52. A method for producing a macromolecule which is capable of exhibiting an excimer effect, which method comprises copolymerizing:
a) one or more excimer forming monomers, the molecules of which are capable of exhibiting an excimer effect when suitably oriented with respect to each other; and
b) one or more other monomers; such that the resulting macromolecule exhibits said excimer effect.

53. The method of claim 52, wherein the macromolecule is capable of detecting the presence or concentration of an analyte.

54. The method of claim 53, wherein
a) the excimer forming monomer individually is not sufficiently water soluble to permit its use in an aqueous environment for detecting the presence or concentration of said analyte; and
b) the other monomer is a hydrophilic monomer; such that the macromolecule is capable of detecting the presence or concentration of said analyte in an aqueous environment.

55. The method of claim 53, wherein the excimer effect does not substantially change in response to changes in the presence or concentration of the analyte.

56. The method of claim 53, wherein
i) the molar ratio of other monomer:excimer forming momomer is from about 2:1 to about 15:1,
ii) the excimer forming monomer comprises an N-(o-boronobenzyl) aminomethylanthracene derivative, and
iii) the other monomer comprises [3-(methacryloylamino) propyl]trimethylammonium chloride.

57. The method of claim 52, wherein the excimer forming monomer is selected from the group consisting of a lanthanide chelate and a polyaromatic hydrocarbon.

58. The method of claim 56, wherein the excimer forming monomer is selected from the group consisting of 9-[[N-methacryloylaminopropyl-N-(o-boronobenzyl) amino]-methyl]anthracene;

9[-N-(2-(5,5-dimethyl-[1,3,2]dioxaborinan-2-yl) benzyl]-N-[3-(methacrylamido) propylamino]methyl]-10-[N-[2-(5,5-dimethyl-[1,3,2]dioxaborinan-2-yl)benzyl]-N-[2-(2-hydroxyethoxy)-ethyl amino]methyl]anthracene;

9-[N-(2-boronobenzyl)-N-[3-(methacrylamido)-propylamino]methyl]-10-(N-(2-boronobenzyl)-N-[2-(2-hydroxyethoxy) ethylamino]methyl]anthracene;

9,10-bis [N-[2-(5,5-dimethyl-[1,3,2]dioxaborinan-2-yl) benzyl]-N-[3-(methacrylamido) propylamino]methyl] anthracene;

9,10-big [N-(2-boronobenzyl)-N-[3-(methacrylamido)-propylamino]methyl]anthracene;

9-[N-[2-(5,5-dimethyl-[1,3,2]dioxaborinan-2-yl)benzyl]-N-[2-(2-methacroyloxyethoxy) ethylamino]methyl]-10-[N-[2-(5,5-dimethyl-[1, 3,2]dioxaborinan-2-yl) benzyl]-N-[2-(2-hydroxyethoxy)-ethylamino]methyl] anthracene;

9-[N-(2-boronobenzyl)-N-[2-(2-methacroyloxyethoxy)-ethylamino]methyl]-10-[N-(2-boronobenzyl)-N-[2-(2-hydroxyethoxy) ethylamino]methyl]anthracene;

9,10-bis [N-[2-(5, 5-dimethyl-[1,3,2]dioxaborinan-2-yl) benzyl]-N-[2-(2-methacroyloxyethoxy) ethylamino] methyl]anthracene;

9,10-bis [N-(2-boronobenzyl)-N-[2-(2-methacroyloxyethoxy) ethylamino]methyl]anthracene; and salts or derivatives thereof.

59. The method of claim 52, wherein the excimer forming monomer is selected from the group consisting of:

N-[3-(methacrylamido)propyl]-3, 4-dihydroxy-9,10-dioxo-2-anthracenesulfonamide;

α,α'-bis[N-[2-(5,5-dimethyl-[1,3,2]dioxaborinan-2-yl) benzyl]-N-[3-(methacrylamido)propylamino]-1,4-xylene; and salts or derivatives thereof.

60. A method for detecting the presence or concentration of an analyte in a sample, said method comprising:
a) exposing the sample to an indicator macromolecule, said macromolecule comprising a copolymer of:
i) one or more indicator component monomers, the molecules of which are capable of exhibiting an excimer effect when suitably oriented with respect to each other, and which are also capable of detecting the presence or concentration of an analyte; and
ii) one or more other monomers; such that the resulting macromolecule exhibits said excimer effect, and wherein the indicator macromolecule has a detectable quality that changes in a concentration-dependent manner when said macromolecule is exposed to said analyte; and
b) measuring any change in said detectable quality to thereby determine the presence or concentration of said analyte in said sample.

61. The method of claim 60, wherein the excimer effect does not substantially change in response to changes in the presence or concentration of the analyte.

62. The method of claim 61, wherein
i) the molar ratio of other monomer:indicator component momomer is from about 2:1 to about 15:1,
ii) the indicator component monomer comprises an N-(o-boronobenzyl) amino]methyl]anthracene derivative, and
iii) the other monomer comprises [3-(methacryloylamino) propyl]trimethylammonium chloride.

63. The method of claim 60, wherein the indicator component monomer is selected from the group consisting of a lanthanide chelate and a polyaromatic hydrocarbon.

64. The method of claim 62, wherein the indicator component monomer is selected from the group consisting of

- 9-[[N-methacryloylaminopropyl-N-(o-boronobenzyl) amino]-methyl]anthracene;
- 9-[N-(2-boronobenzyl)-N-[2-(2-methacroyloxyethoxy)-ethylaminolmethyl]-10-[N-(2-boronobenzyl)-N-[2-(2-hydroxyethoxy) ethylamino]methyl]-anthracene;
- 9,10-bis [N-(2-boronobenzyl)-N-[2-(2-methacroyloxyethoxy) ethylamino]methyl]anthracene;
- 9-[N-[2-(5,5-dimethyl-[1,3,2]dioxaborinan-2-yl)benzyl]-N-[3-(methacrylamido) propylamino]methyl]-10-[N-[2-(5, 5-dimethyl-[1,3,2dioxaborinan-2-yl)benzyl]-N-[2-(2-hydroxyethoxy)-ethylamino]methyl]anthracene;
- 9-[N-(2-boronobenzyl)-N-[3-(methacrylamido)-propylamino]methyl]-10-[N-(2-boronobenzyl)-N-[2-(2-hydroxyethoxy) ethylamino]methyl]anthracene;
- 9,10-bis [N-[2-(5, 5-dimethyl-[1,3,2]dioxaborinan-2-yl) benzyl]-N-[3-(methacrylamido) propylamino]methyl] anthracene;
- 9,10-bis [N-(2-boronobenzyl)-N-]3-(methacrylamido)-propylamino]methyl]anthracene;
- 9-[N-[2-(5,5-dimethyl-[1,3,2]dioxaborinan-2-yl)benzyl]-N-[2-(2-methacroyloxyethoxy) ethylamino]methyl]-10-[N-[2-(5,5-dimethyl-[1,3,2]dioxaborinan-2-yl) benzyl]-N-[2-(2-hydroxyethoxy)-ethylamino]methyl] anthracene;
- 9,10-bis[N-[2-(5,5-dimethyl-[1,3,2]dioxaborinan-2-yl) enzyl]-N-[2-(2-methacroyloxyethoxy) ethylamino] methyl]anthracene; and salts or derivatives thereof.

65. The method of claim 4, wherein the indicator component monomer is selected from the group consisting of:

- N-[3-(methacrylamido)propyl]-3, 4-dihydroxy-9,10-dioxo-2-anthracenesulfonamide;
- α,α'-bis[N-[2-(5,5-dimethyl-[1,3,2]dioxaborinan-2-yl) benzyl]-N-[3-(methacrylamido)propylamino]-1,4-xylene; and salts or derivatives thereof.

* * * * *